United States Patent
Bricker et al.

(10) Patent No.: US 10,370,335 B2
(45) Date of Patent: *Aug. 6, 2019

(54) XANTHURENIC ACID DERIVATIVE PHARMACEUTICAL COMPOSITIONS AND METHODS RELATED THERETO

(71) Applicant: Naturon, Inc., New Canaan, CT (US)

(72) Inventors: Neal S. Bricker, Claremont, CA (US); Stewart Shankel, Redlands, CA (US); Christopher D. Cain, Redlands, CA (US); Mark A. Mitchnick, East Hampton, NY (US); Michael Schmertzler, New Canaan, CT (US)

(73) Assignee: Naturon, Inc., New Canaan, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/249,802

(22) Filed: Apr. 10, 2014

(65) Prior Publication Data
US 2014/0309180 A1  Oct. 16, 2014

Related U.S. Application Data

(63) Continuation of application No. 11/027,131, filed on Dec. 29, 2004, now Pat. No. 8,697,674.

(51) Int. Cl.
*C07D 215/48* (2006.01)
*A61K 31/47* (2006.01)
(Continued)

(52) U.S. Cl.
CPC .......... *C07D 215/48* (2013.01); *A61K 31/341* (2013.01); *A61K 31/47* (2013.01);
(Continued)

(58) Field of Classification Search
CPC ............... C07H 17/02; A61K 2300/00; A61K 31/4706; A61K 31/4709; A61K 31/635;
(Continued)

(56) References Cited

U.S. PATENT DOCUMENTS

| 3,817,837 A | 6/1974 | Rubenstein et al. |
| 4,366,241 A | 12/1982 | Tom et al. |

(Continued)

FOREIGN PATENT DOCUMENTS

| GB | 1 334 705 | 10/1973 |
| GB | 2047691 | 12/1980 |

(Continued)

OTHER PUBLICATIONS

Bricker NS, Biologic and physical characteristics of the non-peptidic, non-digitalis-like natriuretic hormone, Kidney Intl, vol. 44, 1993, 937-947.*

Cain C, Identification of xanthurenic acid 8-o-B-D-glucoside and xanthurenic acid 8-o-sulfate as human natriuretic hormones, PNAS, 2007, 104, 45, 17873-17878.*

Bricker et al., "Biologic and physical characteristics of the non-peptidic, non-digitalis-like natriuretic hormone", *Kidney International*, 44: 937-947 (1993).

Buchli et al., Cloning and functional expression of a soluble form of kynurenine/a-aminoadipate aminotransferase from rat kidney *J. Biol. Chem.* 270 (49): 29330-29335 (1995).

Real and Ferre, "Biosynthesis of xanthurenic acid 8-0-13-D-glucoside in Drosophila" *I Biol. Chem.* 265 (13): 7407-7412 (1990).

Cairns and Payne, "The synthesis of 1-alkyl-1,4-dihydro-4-quinoline-2-carboxylic acids" *J. Heterocyclic Chem.* 15: 551-553 (1978).

Ferre et al., "Xanthurenic acid 8-0-13-D-glucoside, a novel tryptophan metabolite in eye-color mutants of *Drosophila melmogaster*" *J. Biol. Chem.* 260(12): 7509-7514 (1985).

(Continued)

*Primary Examiner* — Kendra D Carter
(74) *Attorney, Agent, or Firm* — Jones Day

(57) ABSTRACT

The present invention relates to diuretic pharmaceutical compositions and methods and in particular to certain derivatives of the formula I

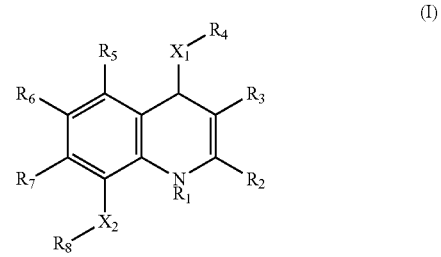

(I)

wherein $R_1$, $R_2$, $R_3$, $R_5$, $R_6$ and $R_7$ are independently $X_3R$ where R is selected from the group consisting of H, halo; optionally substituted saccharide, aliphatic, cycloalkyl, heterocycloalkyl, aryl and heteroaryl; —P(O)(OR$^a$)(OR$^b$) and —NR$^a$R$^b$, where R$^a$ and R$^b$ are independently H, optionally substituted aliphatic, cycloalkyl, heterocycloalkyl, aryl or heteroaryl;

$X_1$, $X_2$ and $X_3$ are independently —C(O)O—, —OC(O)—, —C(O)NH—, —NHC(O)—, —OC(O)NH—, —NHC(O)O—, —OS(O)$_y$—, —S(O)$_y$—, —O—, —NHC(O)—, —NHC(O)O—, —S(O)$_2$NH—, a bond or absent; where y is an integer from 0 to 3; and $R_4$ and $R_8$ are independently H, (=O); hydroxy; or optionally substituted saccharide, aliphatic, cycloalkyl, heterocycloalkyl, aryl or heteroaryl; or —P(O)(OR$^a$)(OR$^b$) or —NR$^a$R$^b$, where R$^a$ and R$^b$ are independently H, or optionally substituted aliphatic, cycloalkyl or heterocycloalkyl, aryl or heteroaryl; or a prodrug or pharmaceutically acceptable salt thereof; and a pharmaceutically acceptable carrier.

20 Claims, 26 Drawing Sheets

(51) Int. Cl.
| | |
|---|---|
| A61K 31/4706 | (2006.01) |
| A61K 31/4709 | (2006.01) |
| A61K 31/341 | (2006.01) |
| A61K 31/675 | (2006.01) |
| A61K 31/706 | (2006.01) |
| A61K 31/54 | (2006.01) |
| A61K 45/06 | (2006.01) |
| C07H 17/02 | (2006.01) |
| G01N 33/53 | (2006.01) |
| G06K 19/02 | (2006.01) |
| G06K 19/077 | (2006.01) |
| A61K 31/635 | (2006.01) |

(52) U.S. Cl.
CPC ...... *A61K 31/4706* (2013.01); *A61K 31/4709* (2013.01); *A61K 31/635* (2013.01); *A61K 31/675* (2013.01); *A61K 31/706* (2013.01); *A61K 45/06* (2013.01); *C07H 17/02* (2013.01); *G01N 33/5308* (2013.01); *G06K 19/02* (2013.01); *G06K 19/0776* (2013.01); *G06K 19/07749* (2013.01)

(58) Field of Classification Search
CPC ...... A61K 31/341; A61K 45/06; A61K 31/47; A61K 31/675; A61K 31/706; C07D 215/48
See application file for complete search history.

(56) References Cited

U.S. PATENT DOCUMENTS

| | | | |
|---|---|---|---|
| 4,376,110 | A | 3/1983 | David et al. |
| 4,552,884 | A | 11/1985 | Sim et al. |
| 4,559,157 | A | 12/1985 | Smith et al. |
| 4,608,392 | A | 8/1986 | Jacquet et al. |
| 4,620,850 | A | 11/1986 | Bachmann et al. |
| 4,656,188 | A | 4/1987 | Verber et al. |
| 4,938,949 | A | 7/1990 | Borch et al. |
| 4,946,778 | A | 8/1990 | Ladner et al. |
| 4,992,478 | A | 2/1991 | Geria |
| 5,106,630 | A | 4/1992 | Bricker et al. |
| 5,124,152 | A | 6/1992 | Biringer et al. |
| 5,738,875 | A * | 4/1998 | Yarwood ............ A61K 9/0056 424/464 |
| 8,034,576 | B2 | 10/2011 | Bricker et al. |
| 2003/0152622 | A1* | 8/2003 | Louie-Helm et al. ........ 424/468 |
| 2004/0157917 | A1 | 8/2004 | Gobaille |
| 2006/0142248 | A1 | 6/2006 | Bricker et al. |
| 2006/0217322 | A1 | 9/2006 | Bricker et al. |
| 2012/0028280 | A1 | 2/2012 | Bricker et al. |

FOREIGN PATENT DOCUMENTS

| | | |
|---|---|---|
| GB | 2 092 130 | 8/1982 |
| JP | 55-151511 | 11/1980 |
| WO | WO 02/15942 A1 | 2/2002 |
| WO | WO 03/005038 A1 | 1/2003 |
| WO | WO-2004/007461 | 1/2004 |
| WO | WO-2007/002781 | 1/2007 |

OTHER PUBLICATIONS

Rocchini et al., "Urinary determination of tryptophan and related metabolites through HPLC in reverse phase" *Rassegna Chimica* 36(1): 15-18 (1984).
Ishiguru et al., "Fluorescent substance in the body of bees" *Yakugaku Zasshi* 94 (1) 116-23 (1974).
Kotake and Murakami, "A possible diabetogenic role for tryptophan matabolites and effects of xanthurenic acid on insulin" *American J. Clinical Nutrition* 24 (7): 826-829(1971).
Bryan et al., "Mouse bladder carcinogenicity of certain tryptophan metabolites and other aromatic nitrogen compounds suspended in cholesterol" *Cancer Research* 24 (4): 596-602 (1964).
Misra and Saxena, "Search for potential amoebicides II. synthesis of substituteed (sulphazino) quinolines" *J. Indian Chem. Soc.* 51 (11): 967-969 (1974).
Misra et al., Search for potential amoebicides: II, synthesis of substituted (—sulphazino) quinolines *Acta Ciencia Indica: Chemistry* 6 (1) 42-45 (1980).
Real and Ferre, "Distribution of xanthurenic acid glucoside in species of the genus *Drosophila*" *Insect Biochemistry* 19(2): 111-116 (1989).
Sato et al., Studies on conjugation of $S^{35}$-sulfate with phenolic compounds *The Journal of Biochemistry (Japan)* 49(2): 164-168 (1961).
Sharma et al., "Synthesis and amoebicidal activity of novel substituted quinolines" *Indian J. Med. Res.* 67: 165-169 (1978).
Shibata et al., "Synthesis of Zeanoside B, a metabolite of IAA in *Zea mays* L." *Agric. Biol. Chem.* 53 (3): 849-850 (1989).
Shirao et al., "Identification of a novel fluorophore, xanthurenic acid 8-0-13-D-glucoside in human brunescent cataract" *Exp. Eye Res.* 73: 421-431 (2001).
Thiagarajan et al., "Role of xanthurenic acid 8-04I-D-glucoside, a novel fluorophore that accumulates in the brunescent human eye lens" *Photochemistry and Photobiology* 76(3): 368-372 (2002).
Soltis et al., *American Journal of Physiology—Regulatory Integrative and Comparative Physiology*, 261:30-32 (1991) (Abtsract only).
Simon et al., "Inhibition of excitatory neurotransmission with kynurenate reduces brain edema in neonatal anoxia", *Neuroscience Letters*, 71 (1986) pp. 361-364.
Yanshole et al., *Phys. Chem. Chem. Phys.* 12:9502-9515 (2010).
Notice of Reasons for Rejection dated Feb. 14, 2012 in corresponding Japanese Patent Application No. 2007-549659 (English translation).
Supplemental European Search Report in corresponding European Patent Application No. 05857253.8 dated Aug. 1, 2012.
Dorwald, F.A., Side Reactions in Organic Synthesis, 2005, Wiley: VCH, Weinheam pg. IX of preface.
Cain et al, "Identification of Xanthurenic acid 8-O-beta-D-glucoside and xanthurenic acid 8-O-sulfate as human natriuretic hormones." PNAS 2007: 104(45); 17873-17878.
Merk Manual, Arterial Hypertension: Merk Manual Professional, http://www.merk.com/mmpe/sec07/ch071/ch071ahtml?qt=diuretics&alt=sh.
Basic and Clinical Immunology, 4th Ed., Chapter 22, "Immunologic Laboratory Tests. Clinical Laboratory Methods for Detection of Antigens and Antibodies" by D. P. Sites et al, published by Lange Medical Publications of Los Altos, Calif., in 1982.
Bird et al., "Single-chain antigen-binding proteins" Science 242:423-26 (1988).
Butler, "The amplified ELISA: Principles and applications for the comparative quantitiation of class and subclass antibodies and the distribution of antibodies and antigens in biochemical separates" Meth. Enzymol., 73:482-523 (1981).
Cole et al., "The EBV-hybridoma technique and its application to human lung cancer" in Monoclonal Antibodies And Cancer Therapy, Alan R. Liss, Inc., New York, pp. 77-96 (1985).
Cote et al., "Generation of human monoclonal antibodies reactive with cellular antigens" *Proc. Nail. Acad Sci. USA*, 80:2026-30 (1983).
D. S. Smith et al., "A Review of Fluoroimmunoassay and Immunofluorometric Assay", Aim. Clin. Biochem. (1981) 18:253-274.
Dias et al., "The EMIT Cyclosporine Assay: development of application protocols for the Boehr nger Mannheim Hitachi 911 and 917 analyzers" Clin. Biochem. Mar. 1997;30 (2):155-62.
Enzyme Immunoassay, edited by E. T. Maggio, "The EMIT-thyroxine assay"; "Enzyme-multiplied technique (EMIT®)", published in 1980 by CRC Press, Inc., Boca Raton, Fla., pp. 141-150, 234-5, and 242-3.
Goodman and Gilman's The Pharmacological Basis for Therapeutics, 10th Ed.; Hardman, Limbird &Gilman, Eds. MacGraw-Hill, p. 772, 2001.

(56) References Cited

OTHER PUBLICATIONS

He et al., "Analysis of diagnostic metabolites by capillary electrophoresis-mass spectrometry" J Chromatogr B Biomed Set AppL Apr. 30, 1999;727(1-2):43-52.

Huse et al., "Generation of a large combinatorial library of the immunoglobulin repertoire in phage lambda" Science, 246:1275-81 (1989).

Huston et al., "Protein engineering of antibody binding sites: recovery of specific activity in an anti-digoxin single-chain Fv analogue produced in *Escherichia coli*" Proc. Natl. Acad Sci. USA, 85:5879-83 (1988).

Kohler and Milstein, "Continuous cultures of fused cells secreting antibody of predefined specificity" Nature, 256:495-7 (1975).

Kozbor et al., "The production of monoclonal antibodies from human lymphocytes" *Immunology Today*, 4:72 (1983).

Marsilio et al., "Simultaneous HPLC determination with light-scattering detection of lactulose and mannitol in studies of intestinal permeability in pediatrics" Clinical Chemistry. ;44:1685-1691 (1998).

Morrison et al., "Chimeric human antibody molecules: mouse antigen-binding domains with human constant region domains" Proc. Natl. Acad. Sci., 81:6851-6855 (1984).

Real and Fent, "Biosynthesis of xanthurenic acid 8-O-b-D-glucoside in *Drosophila*" J. Biol. Chem., 1990, 26503), 7407-7412.

Rich, R.L., et al., "High-resolution and high-throughput protocols for measuring drug/human serum albumin interactions using BIACORE" Analytical Biochemistry, 2001. 296(2): p. 197-207).

Takeda et al., "Construction of chimeric processed immunoglobulin genes containing mouse variable and human constant region sequences" Nature, 314:452-54 (1985).

Theodoridis et al,"Solid-phase microextraction for the analysis of biological samples" J Chromatogr B Blamed Sci Appl. Aug. 4, 2000;745(1):49-82.

Voller et al., "Enzyme immunoassays with special reference to ELISA techiniques" J. Clin. Pathol., 31:507-20 (1978).

Voller, "The Enzyme Linked Immunosorbent Assay (ELISA)"Ric Clin Lab, 8:289-98 (1978).

Ward et al., "Binding activities of a repertoire of a single immunoglobulin variable domains secreted from *Escherichia colt*" Nature, 334:544-46 (1989).

\* cited by examiner

Na⁺ and K⁺ Urine Excretion Response to Synthetic Xanthurenic 8-O-B-glucoside in Normal Sprague Dawley Rat (10.0 ug i.v.)

Na⁺ and K⁺ Urine Concentration in Response to Synthetic Xanthurenic acid 8-O-B-D-glucoside in Normal Sprague Dawley Rat (10.0 ug i.v.)

Na+ and K+ Urine Excretion Response to Synthetic Xanthurenic acid 8-O-B-D-glucoside (10 ug, oral administration) followed by furosemide (100 ug, oral administration) in Normal Sprague Dawley Rat Na+ and K+ Urine Excretion Response to Isolated Xanthurenic acid 8-O-B-D-glucoside (3.0 ug i.v.) followed by Furosemide (20 ug i.v.) in Uremic Sprague Dawley Rat Na⁺ and K⁺ Urine Excretion Response to Isolated Xanthurenic acid 8-sulfate in Uremic Sprague Dawley Rat (2.0 ug i.v.) in Sprague Dawley Rat (2.0 ug i.v.)

Na+ and K+ Urine Concentration Response to Isolated Xanthurenic acid 8-sulfate in Uremic Sprague Dawley Rat (2.0 ug i.v.)

Na+ and K+ Urine Concentration Response to Synthetic Xanthurenic acid 8-O-sulfate (20 ug oral administration) in Normal Sprague Dawley Rat without Saline Infusion Urine Excretion Rate of Normal Sprague Dawley Rat in Response to Furosemide (0.5 mg i.v.)

XANTHURENIC ACID DERIVATIVE PHARMACEUTICAL COMPOSITIONS AND METHODS RELATED THERETO

CROSS-REFERENCE TO RELATED APPLICATIONS

This application is a continuation of U.S. patent application Ser. No. 11/027,131, filed Dec. 29, 2004, pending, the contents of which are incorporated herein by reference.

BACKGROUND OF THE INVENTION

Diuretics are a group of drugs used to treat a variety of medical conditions, including congestive heart failure, hypertension, certain types of liver and kidney diseases and increased intra-ocular pressure. Diuretics act on the transport of sodium ($Na^+$) by the nephrons of the kidney so as to increase the renal excretion of $Na^+$ (and associated ions) and water out of the body and thereby to decrease the extracellular fluid (ECF) volume. Normally, $Na^+$ enters the ECF via the diet, and is excreted in the urine in amounts identical to the intake. In normal adults over 99% of the sodium entering the nephrons of the two kidneys (via glomerular filtration) is transported via an energy dependent process out of the tubular fluid and back into the ECF. When this balance between intake and excretion is upset (with excretion falling below intake) salt retention will occur. A primary mechanism of treating this abnormality involves the administration of one or more agents that reduce $Na^+$ and water reabsorption by the kidneys and thereby increase their excretion in the urine. These agents, collectively, are known as diuretics. Optimally, a powerful diuretic should be natriuretic (inhibit resorption of sodium ions) but not kaliuretic (inhibit resorption of potassium ions) since potassium loss is an undesirable side effect. The principle drugs which are included in the "diuretic" category act by inhibiting the transport of $Na^+$ (and water) out of the tubular fluid by acting on a specific "carrier" in the tubular epithelial cells at a specific site of the nephron. The latter varies with the diuretic employed.

Several major classes of diuretics exist including loop diuretics, thiazide-type diuretics and potassium-sparing diuretics. Loop diuretics, also known as high-ceiling diuretics, act on the thick ascending loop of Henle within the kidney. Examples include furosemide, bumetanide and toresemide. Loop diuretics have a peak diuretic effect far greater than other classes of diuretics. This class acts to inhibit electrolyte reabsorption resulting in the excretion of not only sodium, but also potassium, calcium and magnesium. Loop diuretics are considered "potassium wasting." For example, furosemide is commonly used to treat heart failure, pulmonary edema, hypertension and poisoning. Unfortunately, if dietary potassium is not sufficient, hypokalemia may result and this may induce cardiac arrythmias (Goodman and Gilman's The Pharmacological Basis for Therapeutics, 10th Ed.; Hardman, Limbird & Gilman, Eds. MacGraw-Hill, p. 772, 2001).

Thiazide-type diuretics act in the distal tubule and connecting segment of the kidneys. Examples include chlorothiazide, chlorthalidone, hydrochlorothiazide, indapamide and metolazone. Although thiazides cause less distortion of the electrolyte composition of the extra-cellular fluid than other classes of diuretics, there is also lower intensity of diuresis produced by these drugs. This class contains many sulfonamide chemical entities and thus may cause an allergic reaction in those with sulfa allergies. Although thiazides do not cause calcium excretion, potassium excretion increases with acute administration. Thiazides may also induce hyperglycemia and aggravate pre-existing diabetes mellitus. Thiazide diuretics may also cause increased serum cholesterol, low-density lipoprotein (LDL) and triglyceride concentration. Thiazides are also considered "potassium wasting" diuretics.

Potassium-sparing diuretics may act through either of several mechanisms. Some are steroidal in structure and act in aldosterone-sensitive cells in the cortical connecting tubule in the kidney. Members in this drug class are competitive antagonists of endogenous mineralocorticoid steroids such as aldosterone, which acts to enhance sodium absorption and potassium excretion. The aldosterone receptor is a soluble, cytoplasmic protein found in several tissues including salivary glands, colon and segments of nephrons in the kidney. Spironolactone, a representative member of this drug class, binds to the aldosterone receptor and prevents the receptor from assuming an active conformation. Spironolactone also increases calcium excretion. Common side-effects includes nausea, stomach cramps and diarrhea. Other side effects involve endocrine imbalances, gynecomastia (abnormal enlargement of one or both breasts in men), altered libido, impotence or hirsutism (excessive body hair). Triamterene and amiloride are non-steroidal potassium-sparing diuretics that inhibit electrogenic entry of sodium in the late segments of the kidney nephron. Triamterene and amiloride cause an increase in sodium and chloride excretion, but have little effect on potassium excretion. Side effects of Triamterene include hyperkalemia (increased serum potassium concentration), nausea, vomiting, leg cramps and dizziness. Amiloride side effects also include hyperkalemia, nausea, vomiting, diarrhea and headache.

Other classes of diuretics include osmotic diuretics and carbonic anhydrase inhibitors. Osmotic diuretics, such as mannitol, are poorly reabsorbed by the renal tubules. This drug class effects poor net reabsorption of sodium salts. In addition, mannitol is poorly absorbed by the gastrointestinal tract, and thus must be administered intravenously. Other osmotic diuretics include glycerol, urea and isosorbide.

Carbonic anhydrase inhibitors, such as acetazolamide, cause a modest decrease of sodium reabsorption and may also cause loss of potassium and metabolic acidosis due to its mechanism of action.

Diuretics are used to treat high blood pressure (hypertension), either alone, or in combination with other drugs. High blood pressure adds to the workload of the heart and arteries. If the condition continues for a prolonged period of time, heart and artery function may be impaired. This can damage the blood vessels of the brain, heart and kidneys, resulting in stroke, heart or kidney failure. High blood pressure may also increase the risk of heart attack. These risks can be reduced if blood pressure is properly controlled. The National Heart, Lung, and Blood Institute's (NHLBI) high blood pressure guidelines (JAMA, May 21, 2003; www.nhlbi.nih.gov) emphasize a need to develop new diuretic medications without the side affects of the aforementioned diuretic pharmacopeia.

SUMMARY OF THE INVENTION

A pharmaceutical composition comprising a therapeutically effective amount of a compound of formula I:

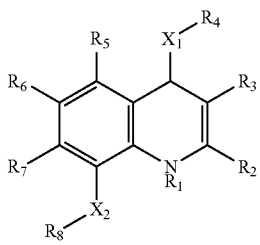

(I)

wherein $R_1$, $R_2$, $R_3$, $R_5$, $R_6$ and $R_7$ are independently $X_3R$ where R is selected from the group consisting of H, halo; optionally substituted saccharide, aliphatic, cycloalkyl, heterocycloalkyl, aryl and heteroaryl; —P(O)(OR$^a$)(OR$^b$) and —NR$^a$R$^b$, where R$^a$ and R$^b$ are independently H, optionally substituted aliphatic, cycloalkyl, heterocycloalkyl, aryl or heteroaryl;

$X_1$, $X_2$ and $X_3$ are independently —C(O)O—, —OC(O)—, —C(O)NH—, —NHC(O)—, —OC(O)NH—, —NHC(O)O—, —OS(O)$_y$—, —S(O)$_y$—, —O—, —NHC(O)—, —NHC(O)O—, —S(O)$_2$NH—, a bond or absent; where y is an integer from 0 to 3; and $R_4$ and $R_8$ are independently H, (=O); hydroxy; or optionally substituted saccharide, aliphatic, cycloalkyl, heterocycloalkyl, aryl or heteroaryl; or —P(O)(OR$^a$)(OR$^b$) or —NR$^a$R$^b$, where R$^a$ and R$^b$ are independently H, or optionally substituted aliphatic, cycloalkyl, heterocycloalkyl, aryl or heteroaryl; or a prodrug or pharmaceutically acceptable salt thereof; and
a pharmaceutically acceptable carrier.

The present invention also provides methods of treating, controlling and preventing hypertension, edema, acute renal failure, congestive heart failure, chronic renal failure, ascites, increased intra-ocular pressure or nephrotic syndrome and other related diseases and conditions using pharmaceutical compositions comprising compounds of formula I.

A BRIEF DESCRIPTION OF THE DRAWINGS

DETAILED DESCRIPTION OF THE INVENTION

Figure 1:
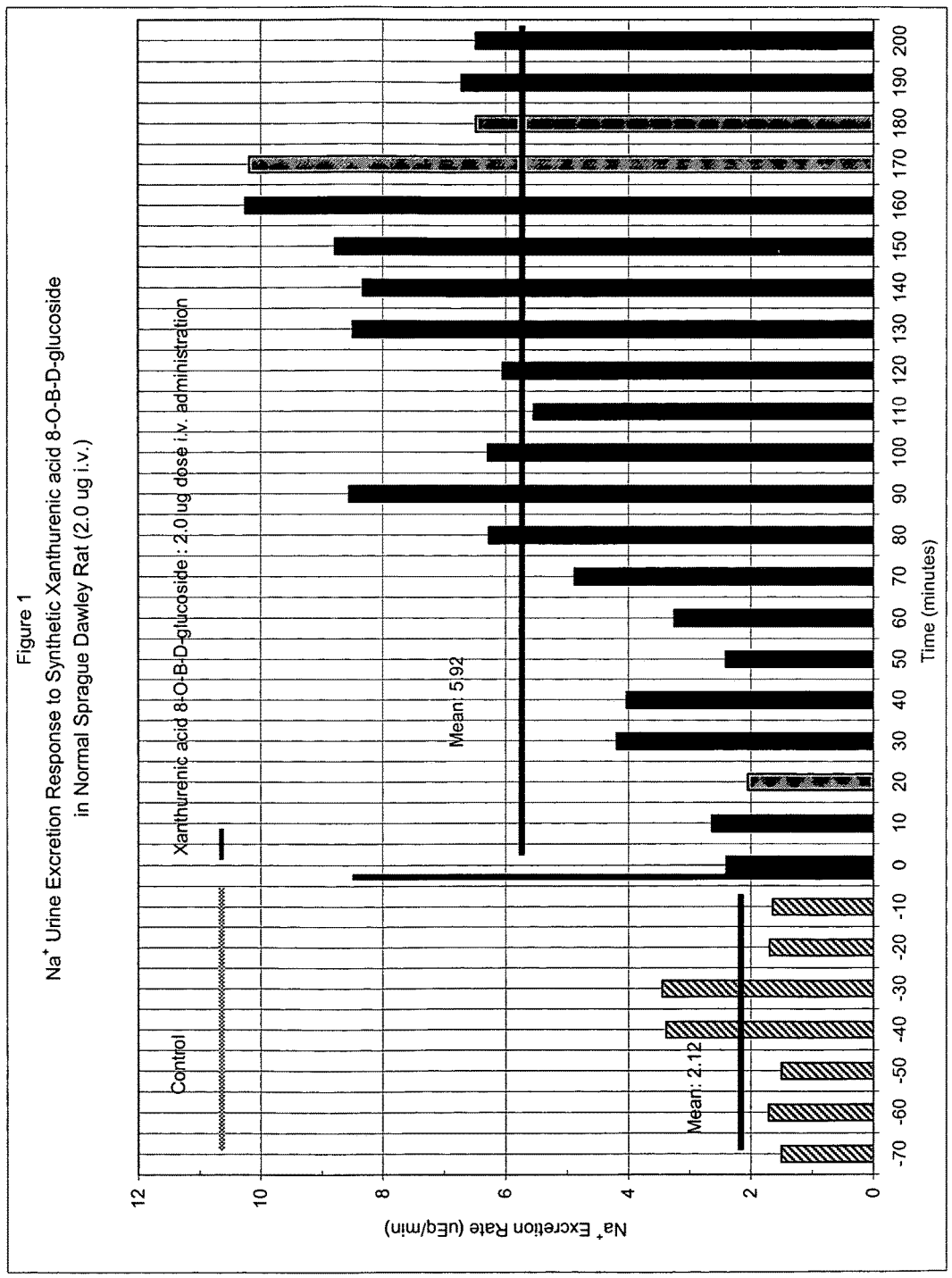
FIG. 1 shows Na$^+$ urine excretion in response to intravenous (i.v.) administration (2 µg dose) of synthetic xanthurenic acid 8-O-ß-D-glucoside in a normal Sprague Dawley rat.
Figure 2:
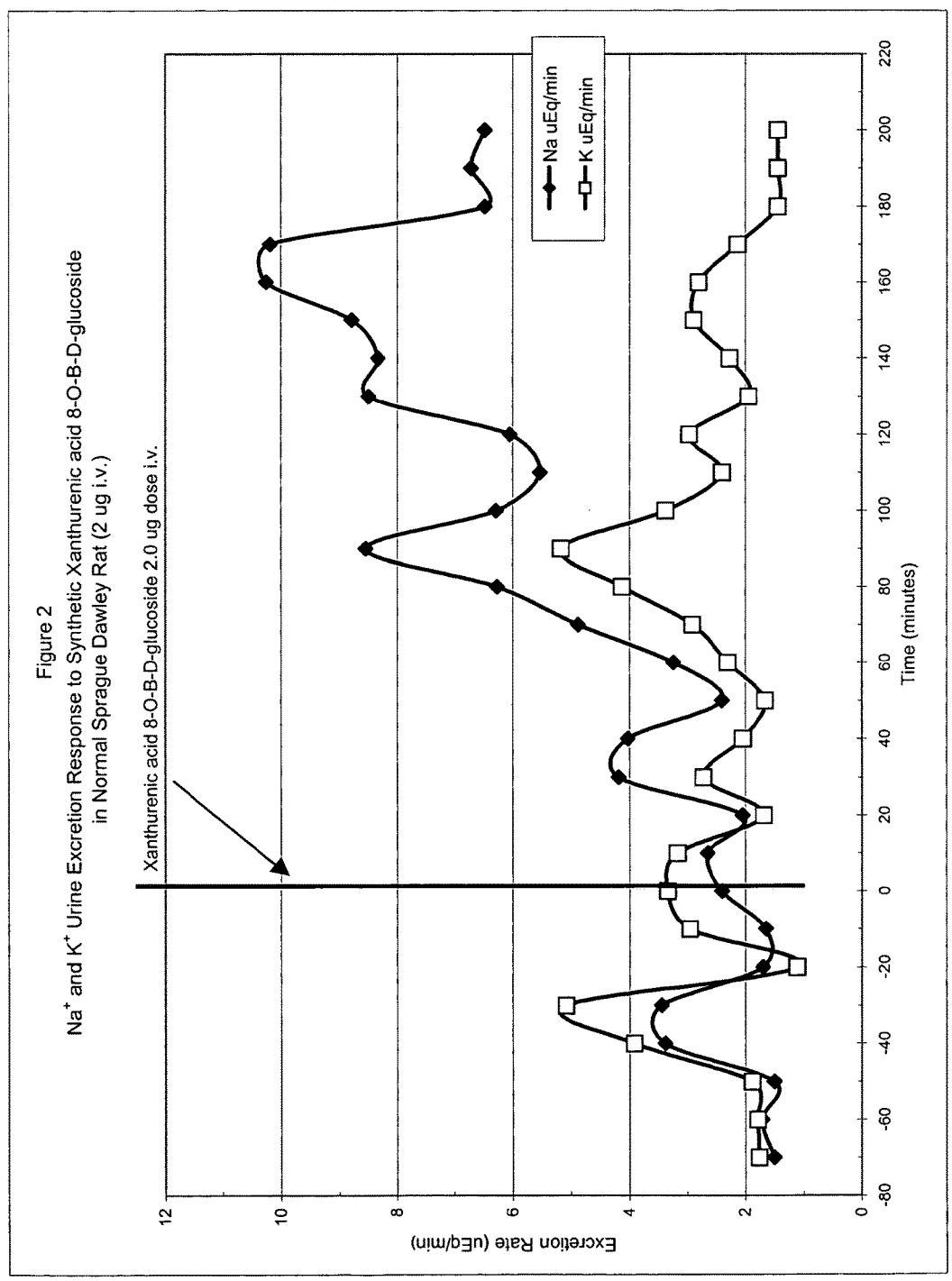
FIG. 2 shows Na$^+$ and K$^+$ urine excretion in response to i.v. administration (2 µg dose) of synthetic xanthurenic acid 8-O-ß-D-glucoside in a normal Sprague Dawley rat.

As used herein, the following definitions shall apply unless otherwise indicated.

The phrase "optionally substituted" is used interchangeably with the phrase "substituted or unsubstituted." Unless otherwise indicated, an optionally substituted group may have a substituent at each substitutable position of the group, and each substitution is independent of any other. Also, combinations of substituents or variables are permissible only if such combinations result in stable compounds. In addition, unless otherwise indicated, functional group radicals are independently selected. Where "optionally substituted" modifies a series of groups separated by commas (e.g., "optionally substituted A, B or C"; or "A, B or C optionally substituted with"), it is intended that each of the groups (e.g., A, B and C) is optionally substituted.

The term "aliphatic" or "aliphatic group" as used herein means a straight-chain or branched $C_{1-12}$ hydrocarbon chain that is completely saturated or that contains one or more units of unsaturation, or a monocyclic $C_{3-8}$ hydrocarbon or bicyclic $C_{8-12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3-7 members. For example, suitable alkyl groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

The terms "alkoxy," "hydroxyalkyl," "alkoxyalkyl" and "alkoxycarbonyl," used alone or as part of a larger moiety include both straight and branched chains containing one to twelve carbon atoms. The terms "alkenyl" and "alkynyl" used alone or as part of a larger moiety shall include both straight and branched chains containing two to twelve carbon atoms.

The terms "haloalkyl," "haloalkenyl" and "haloalkoxy" means alkyl, alkenyl or alkoxy, as the case may be, substituted with one or more halogen atoms. The term "halogen" or "halo" means F, Cl, Br or I.

The term "heteroatom" means nitrogen, oxygen, or sulfur and includes any oxidized form of nitrogen and sulfur, and the quaternized form of any basic nitrogen.

The term "aryl" used alone or in combination with other terms, refers to monocyclic, bicyclic or tricyclic carbocyclic ring systems having a total of five to fourteen ring members, wherein at least one ring in the system is aromatic and wherein each ring in the system contains 3 to 8 ring members. The term "aryl" may be used interchangeably with the term "aryl ring". The term "aralkyl" refers to an alkyl group substituted by an aryl. The term "aralkoxy" refers to an alkoxy group substituted by an aryl.

The term "heterocycloalkyl," "heterocycle," "heterocyclyl" or "heterocyclic" as used herein means monocyclic, bicyclic or tricyclic ring systems having five to fourteen ring members in which one or more ring members is a heteroatom, wherein each ring in the system contains 3 to 7 ring members and is non-aromatic.

The term "heteroaryl," used alone or in combination with other terms, refers to monocyclic, bicyclic and tricyclic ring systems having a total of five to fourteen ring members, and wherein: 1) at least one ring in the system is aromatic; 2) at least one ring in the system contains one or more heteroatoms; and 3) each ring in the system contains 3 to 7 ring members. The term "heteroaryl" may be used interchangeably with the term "heteroaryl ring" or the term "heteroaromatic". Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 3-pyrazolyl, 4-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, and benzoisoxazolyl. The term "heteroaralkyl" refers to an alkyl group substituted by a heteroaryl. The term "heteroarylalkoxy" refers to an alkoxy group substituted by a heteroaryl.

An aryl (including aralkyl, aralkoxy, aryloxyalkyl and the like) or heteroaryl (including heteroaralkyl, heteroarylalkoxy and the like) group may contain one or more substituents. Suitable substituents on the unsaturated carbon atom of an aryl, heteroaryl, aralkyl or heteroaralkyl group are selected from halogen; haloalkyl; —$CF_3$; —$R^9$; —$OR^9$; —$SR^9$; 1,2-methylenedioxy; 1,2-ethylenedioxy; protected OH (such as acyloxy); phenyl (Ph); Ph substituted with $R^9$; —O(Ph); —O—(Ph) substituted with $R^9$; —$CH_2$(Ph); —$CH_2$(Ph) substituted with $R^9$; —$CH_2CH_2$(Ph); —$CH_2CH_2$(Ph) substituted with $R^9$; —$NO_2$; —CN; —$NR^9R^{10}$; —$NR^9C(O)R^{10}$; —$NR^9C(O)NR^{10}R^{11}$; —$NR^9CO_2R^{10}$; —$NR^9NR^{10}C(O)R^{11}$; —$NR^9$—$NR^{10}C(O)NR^{11}R^{12}$; —$NR^9NR^{10}CO_2R^{11}$; —C(O)C(O)$R^9$; —C(O)$CH_2C(O)R^9$; —$CO_2R^9$; —C(O)$R^9$; —C(O)$NR^9R^{10}$; —OC(O)$NR^9R^{10}$; —S(O)$_2R^9$; —$SO_2NR^9R^{10}$; —S(O)$R^9$; —$NR^9SO_2NR^{10}R^{11}$; —$NR^9SO_2R^{10}$; —C(=S)$NR^9R^{10}$; —C(=NH)—$NR^9R^{10}$; —$(CH_2)_yNHC(O)R^9$; —$(CH_2)_yR^9$; —$(CH_2)_yNHC(O)NHR^9$; —$(CH_2)_yNHC(O)OR^9$; —$(CH_2)_yNHS(O)R^9$; —$(CH_2)_yNHSO_2R^9$ or —$(CH_2)_yNHC(O)CH((V)_z$—$R^9)(R^{10})$ wherein $R^9$, $R^{10}$, $R^{11}$ and $R^{12}$ are independently selected from hydrogen, optionally substituted $C_{1-6}$ aliphatic, an unsubstituted 5-6 membered heteroaryl or heterocyclic ring, phenyl (Ph), —O(Ph) or —$CH_2$(Ph)-$CH_2$(Ph), wherein y is 0-6; z is 0-1; and V is a linker group. When $R^9$, $R^{10}$, $R^{11}$ or $R^{12}$ is $C_{1-6}$ aliphatic, it may be substituted with one or more substituents selected from —$NH_2$, —NH($C_{1-4}$ aliphatic), —N($C_{1-4}$ aliphatic)$_2$, —S(O)($C_{1-4}$ aliphatic), —$SO_2(C_{1-4}$ aliphatic), halogen, ($C_{1-4}$ aliphatic), —OH, —O—($C_{1-4}$ aliphatic), —$NO_2$, —CN, —$CO_2H$, —$CO_2(C_{1-4}$ aliphatic), —O(halo $C_{1-4}$ aliphatic), or -halo($C_{1-4}$ aliphatic); wherein each $C_{1-4}$ aliphatic is unsubstituted.

An aliphatic group or a non-aromatic heterocyclic ring may contain one or more substituents. Suitable substituents on the saturated carbon of an alkyl group or of a non-aromatic heterocyclic ring are selected from those listed above for the unsaturated carbon of an aryl or heteroaryl group and the following: =O, =S, =$NNHR^{13}$, =$NNR^{13}R^{14}$, =N—, =$NNHC(O)R^{13}$, =$NNHCO_2$(alkyl), =$NNHSO_2$(alkyl), or =$NR^{13}$, where $R^{13}$ and $R^{14}$ are independently selected from hydrogen and an optionally substituted $C_{1-6}$ aliphatic. When $R^{13}$ or $R^{14}$ is $C_{1-6}$ aliphatic, it may be substituted with one or more substituents selected from —$NH_2$, —NH($C_{1-4}$ aliphatic), —N($C_{1-4}$ aliphatic)$_2$, halogen, —OH, —O—($C_{1-4}$ aliphatic), —$NO_2$, —CN, —$CO_2H$, —$CO_2(C_{1-4}$ aliphatic), —O(halo $C_{1-4}$ aliphatic) or -halo($C_{1-4}$ aliphatic); wherein each $C_{1-4}$ aliphatic is unsubstituted.

Substituents on the nitrogen of a non-aromatic heterocyclic ring are selected from —$R^{15}$, —$NR^{15}R^{16}$, —C(O)$R^{15}$, —$CO_2R^{15}$, —C(O)C(O)$R^{15}$, —C(O)$CH_2C(O)R^{15}$, —$SO_2R^{15}$, —$SO_2NR^{15}R^{16}$, —C(=S)$NR^{15}R^{16}$, —C(=NH)$NR^{15}R^{16}$ or —$NR^{15}SO_2R^{16}$; wherein $R^{15}$ and $R^{16}$ are independently selected from hydrogen, an optionally substituted $C_{1-6}$ aliphatic, optionally substituted phenyl (Ph), optionally substituted —O(Ph), optionally substituted —CH$_2$(Ph), optionally substituted —CH$_2$CH$_2$(Ph), or an unsubstituted 5-6 membered heteroaryl or heterocyclic ring. When R$^{15}$ or R$^{16}$ is a C$_{1-6}$ aliphatic group or a phenyl ring, it may be substituted with one or more substituents selected from —NH$_2$, —NH(C$_{1-4}$ aliphatic), —N(C$_{1-4}$ aliphatic)$_2$, halogen, —(C$_{1-4}$ aliphatic), —OH, —O—(C$_{1-4}$ aliphatic), —NO$_2$, —CN, —CO$_2$H, —CO$_2$(C$_{1-4}$ aliphatic), —O(halo C$_{1-4}$ aliphatic) or -halo(C$_{1-4}$ aliphatic); wherein each C$_{1-4}$ aliphatic is unsubstituted.

The term "saccharide" defines a carbohydrate, or sugar, made up of one or more units with the empirical generic formula (CH$_2$O)$_n$. A saccharide is further classified as a monosaccharide, disaccharide or polysaccharide depending on the number of units or a aminosaccharide if one or more oxygen atoms are replaced by a nitrogen atom. A saccharide may also be classified as a deoxysaccharide if one or more hydroxy groups are replaced by a hydrogen atom.

A saccharide substituent may be further substituted on any primary or secondary hydroxy group by, for example, an alkyl, alkoxyalkyl, aryl, heteroaryl, ether, ester, acetal, carbonate or carbamate.

The term "monosaccharide" defines a single carbohydrate, or sugar unit. Two families of monosaccharides are aldoses or ketoses. Aldoses have a carbonyl group at the end of the carbon chain as an aldehyde, when the monosaccharide is written in a linear, open-chain formula. If the carbonyl is in any other position in the carbon chain the monosaccharide is a ketone and referred to as a ketose. Three carbon monosaccharides are trioses: glyceraldehydes, an aldose, and dihydroxyacetone, a ketose. Monosaccharides, except for dihydroxyacetone, have one or more asymmetric centers. The prefixes D- or L- refer to the configuration of the carbon atom of the chiral carbon most distant from the carbonyl carbon. Monosaccharides with 4, 5, 6 and 7 carbon atoms in their backbones are termed tetroses, pentoses, hexoses, and heptoses, respectively. Each of these exists in two series: aldotetroses and ketotetroses, aldopentoses and ketopentoses, aldohexoses and ketohexoses, aldoheptoses and ketoheptoses. Tetroses include erythrose and threose. Pentoses include ribose, arabinose, xylose and lyxose. Hexoses include allose, altrose, glucose, mannose, gulose, idose, galactose and talose. Monosaccharides with 5 or more carbons in the backbone usually occur as cyclic, or ring, structures in which the carbonyl carbon has formed a covalent bond with one of the hydroxy groups along the chain. Six-membered ring compounds are termed pyranoses, five-membered ring compounds are furanoses. Formation of a six-membered ring results from reaction of aldehydes and alcohols to form hemi-acetals which contain an asymmetric carbon atom. One configuration around is described as α- and the other is described as the β-form.

The term "disaccharide" refers to a molecular moiety containing two monosaccharides covalently bound to each other. Disaccharides include maltose [glucose-glucose], lactose [galactose-glucose] and sucrose [fructose-glucose].

The term "polysaccharide" includes multiple monosaccharides units covalently bound to each other. Polysaccharides include starch, hyaluronic acid, amylase, amylopectin, dextran, cyclodextrin and glycogen.

The term "aminosaccharide" refers to a carbohydrate molecule where one or more hydroxy groups are replaced by an amino group. This includes the monosaccharides glucosamine and muramic acid and the polysaccharide chitin. The amino groups may be acetylated to include N-acetyl-D-glucosamine and N-acetyl-D-muramic acid.

The term "deoxysaccharide" refers to a carbohydrate molecule where one or more hydroxy groups are replaced by hydrogen. These include, for example, L-rhamnose (6-deoxy-L-mannose), L-fucose (6-deoxy-L-galactose) and D-fucose (rhodeose).

The term "treatment" refers to any treatment of a pathologic condition in a mammal, particularly a human, and includes: (i) preventing the pathologic condition from occurring in a subject which may be predisposed to the condition but has not yet been diagnosed with the condition and, accordingly, the treatment constitutes prophylactic treatment for the disease condition; (ii) inhibiting the pathologic condition, i.e., arresting its development; (iii) relieving the pathologic condition, i.e., causing regression of the pathologic condition; or (iv) relieving the conditions mediated by the pathologic condition.

The term "therapeutically effective amount" refers to that amount of a compound of the invention that is sufficient to effect treatment, as defined above, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "pharmaceutically acceptable salts" includes, but is not limited to, salts well known to those skilled in the art, for example, mono-salts (e.g. alkali metal and ammonium salts) and poly salts (e.g. di- or tri-salts,) of the compounds of the invention. Pharmaceutically acceptable salts of compounds of formula I are where, for example, an exchangeable group, such as hydrogen in —OH or —NH— is replaced with a pharmaceutically acceptable cation (e.g. a sodium, potassium, or ammonium ion) and can be conveniently be prepared from a corresponding compound of formula I by, for example, reaction with a suitable base. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example, calcium) salts of carboxylic acids can also be made.

The term "disease," "disorder" or "condition" as used herein, means any disease or other deleterious condition or disease in which therapeutic administration of a diuretic drug, or pharmaceutical composition, is known to play a role in treatment thereof. Such diseases or conditions include, without limitation, hypertension, edema, acute renal failure, congestive heart failure, chronic renal failure, ascites, intraocular pressure or nephrotic syndrome and complications due to or exacerbated by those conditions.

The term "diuretic" as used herein, means a drug or other substance tending to promote the formation and excretion of urine.

The term "hypertension" as used herein, refers to a disorder characterized by elevated blood pressure.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of hydrogen by a deuterium or tritium, or the replacement of a carbon by a $^{13}$C- or $^{14}$C-enriched carbon are within the scope of this invention.

One aspect of the present invention relates to pharmaceutical compositions comprising compounds of formula I. In one preferred embodiment, the composition comprises compounds of formula I wherein $R_1$, $R_3$, $R_5$, $R_6$ and $R_7$ are independently H, halogen or lower alkyl. In another, $X_1$ is absent and $R_4$ is (=O); or $X_1$ is a bond and $R_4$ is hydroxy. In another embodiment, $X_1R_4$ is —OC(O)CH$_3$. In another embodiment, $R_2$ is —C(O)OR where R is preferably H or optionally substituted alkyl where alkyl may be methyl, ethyl, butyl, octyl or undecyl. In another embodiment, $R_2$ is —C(O)NHR where R is preferably H or optionally substituted alkyl, cycloalkyl, heterocycloalkyl, aryl or heteroaryl.

In one embodiment of the invention, $X_2$ is —O— and $R_8$ is an optionally substituted saccharide, preferably a monosaccharide selected from an aldohexopyranose, aldopentopyranose, aldopentofuranose or ketose. In other embodiments, $R_8$ is D-galactose, D-mannose, D-ribose, D-fucose or L-rhamnose. In a preferred embodiment, $R_8$ is D-glucose. In one specific embodiment, the compound of formula I is xanthurenic acid 8-O-β-D-glucoside.

In another embodiment, $X_2$ is —O— and $R_8$ is —CH$_2$CO$_2$R or —CH$_2$C(O)NHR where R is preferably H or optionally substituted alkyl, cycloalkyl, heterocycloalkyl, aryl or heteroaryl.

According to another embodiment of the invention, the pharmaceutical composition comprises a compound of formula I where $X_2R_8$ is an acyl, phosphate, phosphonic acid, alkyl phosphonate or a sulfate group. In one specific embodiment, the compound is xanthurenic acid 8-O-sulfate.

The invention further provides a pharmaceutical composition comprising a therapeutically effective amount of a compound represented by formula I in combination one or more additional diuretic compounds or cardiovascular agents; and a pharmaceutically acceptable carrier.

The pharmaceutical compositions described herein are useful for treatment or prevention of hypertension, edema, acute renal failure, congestive heart failure, chronic renal failure, ascites, intra-ocular pressure or nephrotic syndrome and complications due to or exacerbated by those conditions.

Depending upon the particular condition to be treated or prevented, additional therapeutic agents, which are normally administered to treat or prevent that condition, may be administered together with the compounds of this invention. For example, in the treatment of hypertension, one or more additional diuretic compounds or cardiovascular agents may be combined with the compounds of this invention to treat hypertension. The additional diuretic agent is selected from the group consisting of a loop diuretic, thiazide diuretic, potassium-sparing diuretic, carbonic anhydrase inhibitor and osmotic diuretic. The cardiovascular agent is selected from the group consisting of an angiotensin converting enzyme inhibitor, angiotensin II receptor antagonist, beta-adrenergic blocker, calcium channel blocker, cholesterol altering drug, triglyceride lowering agent, c-reactive protein lowering agent, homocysteine lowering agent, aspirin and its derivatives, ionotropic agent, antiarrhythmic agent and blood thinner (anticoagulant). These agents include, without limitation, furosemide, bumetanide, torsemide, ethacrynic acid, chlorothiazide, hydrochlorothiazide, spironolactone, amiloride, triamterene, acetazolamide, methazolamide, dichlorphenamide, hydroflumethiazide, methyclothiazide, indapamide, metolazone, polythiazide, chlorthalidone, dorzolamide, brinzolamide, glycerol, mannose, urea, lisinopril, moexipril, enalapril, irbesartan, valsartan, losartan, nadolol, propranolol, atenolol, timolol and bisoprolol.

The compounds of formula I can be formulated as pharmaceutical compositions and administered to a mammalian host, such as a human patient, in a variety of forms adapted to a selected route of administration, i.e., by oral, parenteral, intravenous, intramuscular, topical, or subcutaneous routes. Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms. The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions. For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

The present compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops, etc. Topical applications may be formulated in hydrophobic or hydrophilic bases as ointments, creams, lotions, paints, powders, etc.

For veterinary medicine, the composition may, for example, be formulated as an intra-mammary preparation in either long acting or quick-release bases.

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The compositions per unit dosage, whether liquid or solid may contain from 0.1% to 99% of active material (compound I or salts thereof), the preferred range being from about 10-60%. The composition will generally contain from about 15 mg to about 1,500 mg by weight of active ingredient based upon the total weight of the composition; however, in general, it is preferable to employ a dosage amount in the range of from about 250 mg to 1,000 mg. In parenteral administration the unit dosage is usually the pure compound in a slightly acidified sterile water solution or in the form of a soluble powder intended for solution. Single dosages for injection, infusion or ingestion may be administered, i.e., 1-3 times daily, to yield levels of about 0.5-50 mg/kg, for adults.

The invention will now be described in greater detail by reference to the following non-limiting examples.

EXAMPLES

Example 1. Synthesis of Xanthurenic Acid 8-O-β-D-Glucoside

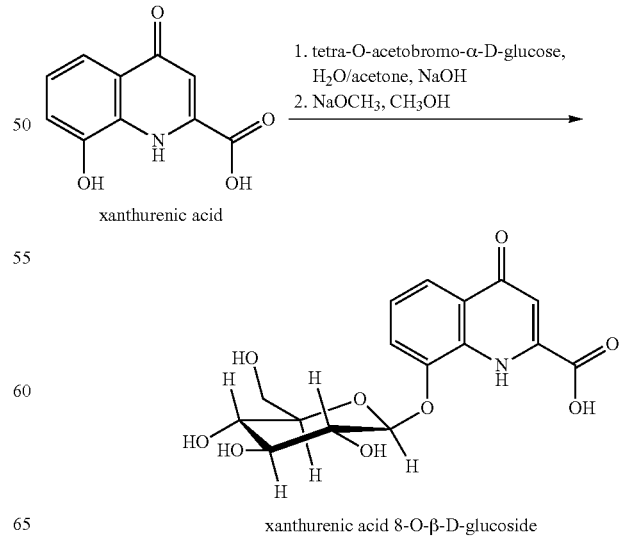

Step 1: Synthesis of xanthurenic acid 2,3,4,6-tetra-O-acetyl 8-O-β-D-glucoside. (See, for example, Real, et al., J. Biol. Chem., 1990, 265(13), 7407-7412)

Xanthurenic acid was obtained commercially from Aldrich, Milwaukee, Wis. Xanthurenic acid (930 mg, 4.53 mmol) in aqueous 1M NaOH (10 mL) was cooled to 10° C. 2,3,4,6-tetra-O-acetyl8-α-D-glucopyranosylbromide (2.03 g, 4.94 mmol) in acetone (16 mL) was added dropwise over 10 minutes. The solution was allowed to warm to room temperature over 4 hours. Additional aqueous 1M NaOH (3 mL) was added slowly over 30 minutes and solution stirred 30 minutes. The mixture was extracted with water and diethyl ether. The aqueous portion was acidified to pH 3.5 and further extracted with 1:1 tetrahydrofuran/ethylacetate. The combined organic layers were washed with saturated aqueous NaCl and dried over magnesium sulfate. Following filtration, the crude xanthurenic acid tetra-O-acetyl 8-β-D-glucoside intermediate was concentrated in vacuo to give approximately 1 gram of a crude residue. The residue was triturated with 4:1 dimethylsulfoxide/water (28 mL), filtered and dried to return 215 mg of xanthurenic acid tetra-O-acetyl 8β-D-glucoside as an off-white solid intermediate. The mother liquor was further purified by high-pressure liquid chromatography (HPLC) to recover an additional 60 mg of intermediate (C18, water/acetonitrile with 0.2% trifluoroacetic acid; step elution) for a combined 11.5% yield. $^1$H NMR (300 MHz, DMSO-$d_6$) δ 1.97 (s, 3H), 1.99 (s, 3H), 2.00 (s, 3H), 2.06 (s, 3H), 4.05-4.30 (m, 3H), 5.07 (d, J=9.6 Hz, 1H), 5.23 (dd, J=9.6, 7.8 Hz, 1H), 5.44 (t, J=9.60 Hz, 1H), 5.67 (d, J=7.8 Hz, 1H), 6.65 (s, 1H), 7.37 (t, J=8.1 Hz, 1H), 7.48 (dd, J=7.5, 1.2 Hz, 1H), 7.81 (dd, J=8.1, 1.2 Hz, 1H), 9.44 (bs, 1H). ESI-MS m/z 536.44 (M+H$^+$).

Step 2: Xanthurenic acid 8-O-β-D-glucoside.

Xanthurenic acid 2,3,4,6-tetra-O-acetyl 8-O-β-D-glucoside from step 1 (190 mg, 0.35 mmol) was added to a solution of 95% sodium methoxide (40 mg, 0.7 mmol) in methanol (5 mL). The mixture was stirred for one hour. The mixture was adjusted to pH 3.5 with aqueous 1M HCl. The slurry was diluted with 20 mL diethyl ether and filtered. The filter cake was washed with 1:1 methano/diethyl ether and dried in vacuo to give 118 mg of xanthurenic acid 8-O-β-D-glucoside in an 82% yield. FTIR (neat) 3000-3700 (br s), 3365, 2934, 1626, 1602 cm$^{-1}$. $^1$H NMR (300 MHz, DMSO-$d_6$) δ 3.10-3.70 (m, 6H and H$_2$O), 4.87 (d, J=7.5 Hz, 1H), 4.95 (m, 1H), 5.16 (m, 1H), 5.33 (m, 1H), 5.81 (m, 1H), 6.47 (s, 1H), 7.21 (t, J=8.0 Hz, 1H), 8.07 (d, J=7.2 Hz, 1H), 8.24 (dd, J=8.4, 1.0 Hz, 1H), 8.47 (s, <1H, partial exchange), 10.47 (br s, 1H). $^{13}$C-NMR (75.4 MHz, DMSO-$d_6$) δ 60.74, 69.62, 73.49, 76.56, 77.66, 103.73, 107.73, 119.65, 122.72, 126.79, 132.00, 146.24, 147.05, 162.85, 166.88, 178.33. Electrospray ionization mass spectra (ESI-MS) m/z 368.31 (M+H$^+$).

Example 2. Synthesis of Xanthurenic Acid 8-O-Sulfate

Scheme 2: Synthesis of Xanthurenic acid 8-O-sulfate.

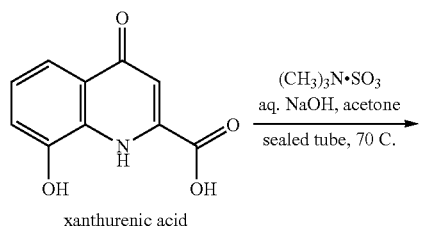

xanthurenic acid

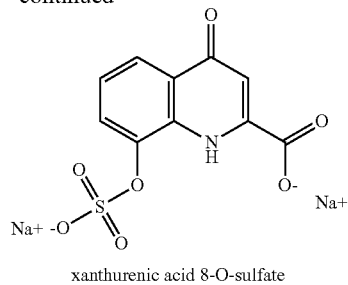

xanthurenic acid 8-O-sulfate

To a solution of xanthurenic acid (300 mg, 1.46 mmol) in 2.9 mL of 1N NaOH and 2.1 mL of dH$_2$O (deionized water) were added sulfertrioxide trimethylamine (407 mg, 2.92 mmol) and 5 mL of acetone at room temperature. The reactor (20×125 mm tube) was sealed under nitrogen and stirred at 70° C. for 16 hours. The reaction was cooled to room temperature and concentrated to dryness under reduced pressure. The residue was washed with acetone, acetonitrile, dichloromethane, ethyl acetate and then diethyl ether consecutively. The collected solid was placed under vacuum overnight. The solid was dissolved in 3 mL dH$_2$O, loaded to a Sephadex SP-C25 column (4×11 cm, 40-125μ) and eluted with dH$_2$O to afford the sodium salt of the title compound (474 mg, 1.44 mmol) in a 98.8% yield as a shiny brown powder with mp>250° C. (dec.). $^1$H NMR (300 MHz, D$_2$O) δ 6.67 (br s, 1H), 7.28 (br dd, J=8.1, 7.8 Hz, 1H), 7.56 (br d, J=7.8 Hz, 1H), 7.79 (br d, J=8.1 Hz, 1H). $^{13}$C NMR (75 MHz, D$_2$O) δ 108.5, 122.1, 124.9 125.6, 126.1, 132.6 140.7, 144.7, 166.3, 181.0. IR (solid, cm$^{-1}$) 2835, 2545, 1687, 1601, 1372, 1372, 1254.

Example 3. Isolation of Xanthurenic Acid 8-O-Sulfate and Xanthurenic Acid 8-O-β-D-Glucoside Urine samples from human uremic patients were collected over 24-hour periods. The typical collection volume was of 2-3 liters per patient. Individual samples were lyophilized to dryness and reconstituted with 100 mL of deionized water. The reconstituted samples (25 mL load volume) were size-fractionated using gel filtration Sephadex G-25 column chromatography with elution by 10 mM ammonium acetate, pH 6.8 at 10° C. and monitored by UV at 285 nm and conductivity. Later eluting (post-salt peak) 10 mL fractions with LTV activity and osmolality<100 mOsm were screened for biological activity with the frog skin assay of Bricker et al. (Kidney International Vol. 44 (1993) November; 44 (5): 937-47). Fractions with activity (10 mL each) were concentrated by lyophilization and reconstituted with 1 mL dionized water.

Reconstituted Sephadex G-25 fractions with biological activity were further fractionated with high performance liquid chromatography (HFLC; 1 mL load volume) over an octadecylsilyl (Phenomenex SphereClone ODS2, 35° C.) semi-preparative HPLC column at 4 mL/minute with a 0.1 M pyridium acetate: methanol gradient; 0-40% methanol/11 minutes with collection of 2 mL fractions. Elution was monitored by fluorescence (excitation 332 nm, emission at 430 nm) and UV (338 nm). Fractions with a retention time (RT) of 12.4 minutes were pooled from multiple runs and concentrated approximately 10-fold. The fractions were re-applied to the HPLC system above with a 1 mL injection volume run in isocratic mode with 92% 0.1 M/8% methanol at 4 mL/minute. Fluorescence was monitored with excitation 332 nm, emission 430 nm. UV was monitored at 338 nm. These maxima are for xanthurenic acid 8-O-ß-D-glucoside. Eluate between 10-13 minutes was collected in 12 second (0.8 mL) fractions. Fractions eluting between 11.2-11.6 minutes RT contained xanthurenic acid 8-O-β-D-glucoside; fractions eluting between 12.0-12.5 minutes contained xanthurenic acid 8-O-sulfate. Fractions containing either the xanthurenic acid 8-O-β-D-glucoside or the xanthurenic acid 8-O-sulfate were separately pooled and concentrated on a Savant Speed-Vac Plus (SC210A) with medium heat. The pools were resubjected to isocratic HPLC on an analytical scale using a reverse phase C-18 HPLC column: Phenomenex P/NO 00G-4375-E0, SYNERGI 4u Hydro-RP 80A 250×4.6 mm, 4 micron. The HPLC purification was run in isocratic mode at 1 mL/minute with 8% methanol and 0.1% 0.1M pyridium acetate at 35° C. Elution was monitored by UV absorbance at 338 nm and fluorescence detection with excitation 332 nm, emission 430 nm. Fractions containing xanthurenic acid 8-O-β-D-glucoside had RT=10.2-10.6 minutes. Fractions from separate xanthurenic acid 8-O-sulfate runs had RT=11-11.5 minutes. Fractions were pooled and concentrated on a Speed-Vac, with occasional addition of pyridine to increase pH. The purified xanthurenic acid 8-O-β-D-glucoside was reapplied to the same analytical column and eluted with 20% methanol in water to eliminate pyridium acetate. Xanthurenic acid 8-O-β-D-glucoside formed crystals upon concentration by this technique. For isolated xanthurenic acid 8-O-β-D-glucoside ($C_{16}H_{17}NO_9$): ESI-MS (m/z) 367.09, 368.094 (M+H) and 229 (M-glucose+Na+); $^1$H-NMR (500 MHz, $D_2O$) δ 3.58 (dd, J=9, 9.5 Hz, 1H), 3.65 (dd, J=9, 9.5 Hz, 1H), 3.67 (m, 1H), 3.80 (dd, 1H), 3.81 (dd, J=8, 9.5 Hz), 3.95 (dd, 1H), 5.24 (d, J=8 Hz, 1H), 6.93 (s, 1H), 7.47 (t, J=8 Hz, 1H), 7.59 (dd, J=8, 2 Hz, 1H), 7.90 (dd, J=8, 2 Hz) ppm; $^{13}$C-NMR (126 MHz, $D_2O/CD_3OD$) δ 60.8, 69.7, 72.9, 75.7, 76.7, 101.2, 108.1, 117.9, 118.2, 124.5, 125.2, 130.6, 143.9, 145.5, 165.9, 180.3 ppm. For isolated xanthurenic acid 8-O-sulfate ($C_{10}H_7NO_7S$): ESI-MS (m/z) 284.994, 285.998 (M+H+).

Figure 3:
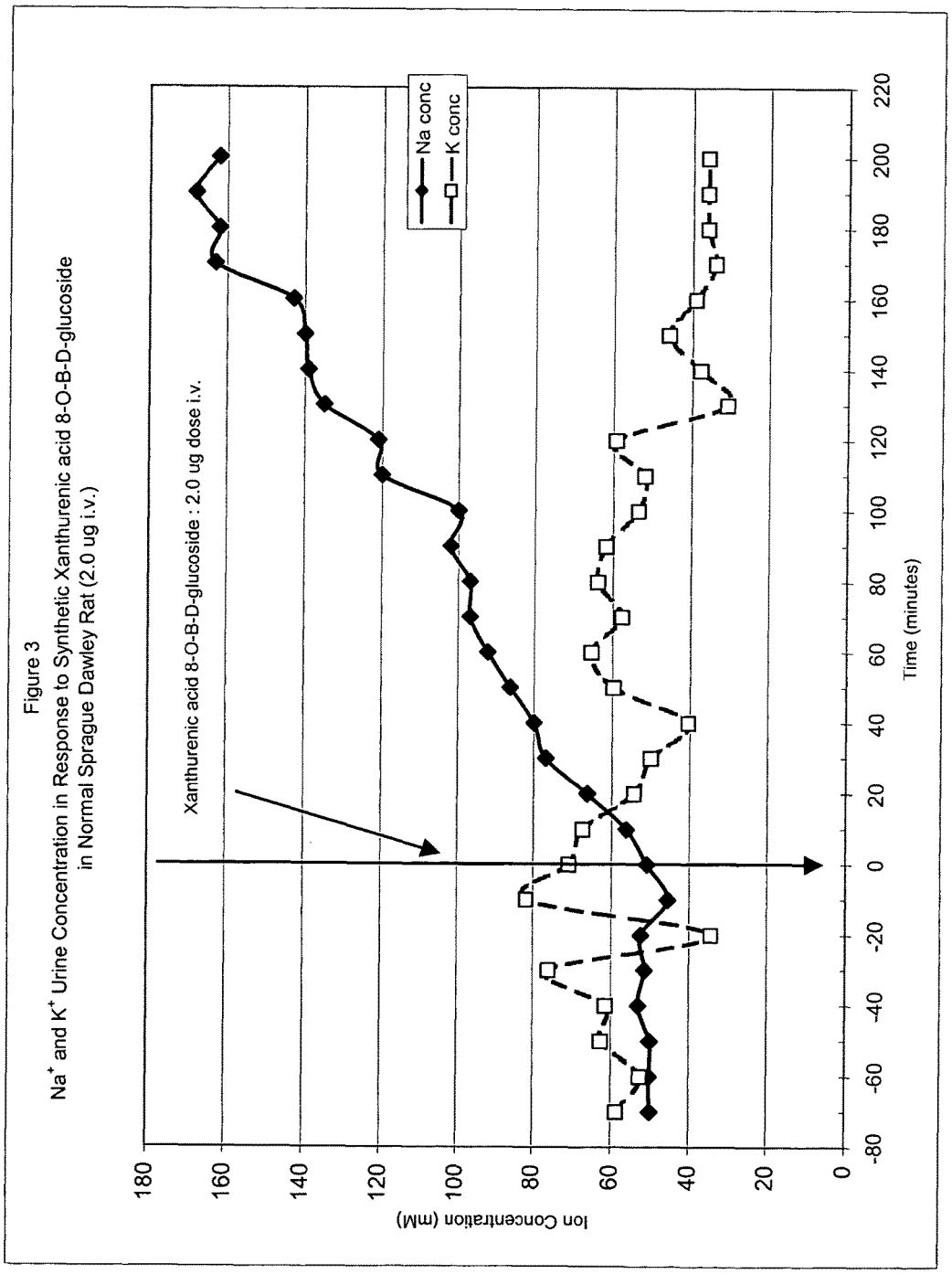
FIG. 3 shows Na$^+$ and K$^+$ concentration in urine following i.v. administration (2 µg dose) of synthetic xanthurenic acid 8-O-ß-D-glucoside in a normal Sprague Dawley rat.
Figure 4:
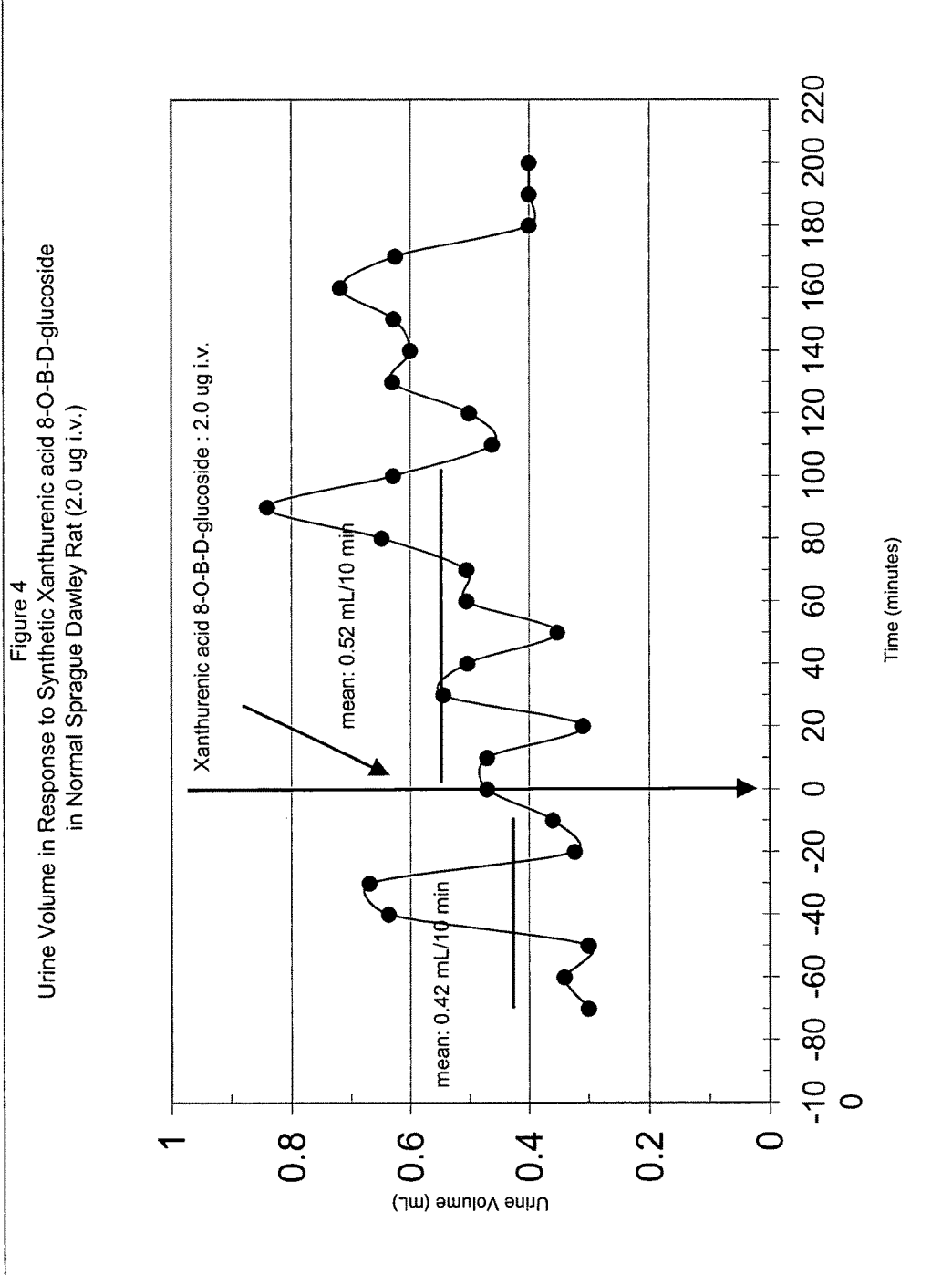
FIG. 4 shows urine volume following i.v. administration (2 µg dose) of synthetic xanthurenic acid 8-O-ß-D-glucoside in a normal Sprague Dawley rat.
Figure 5:
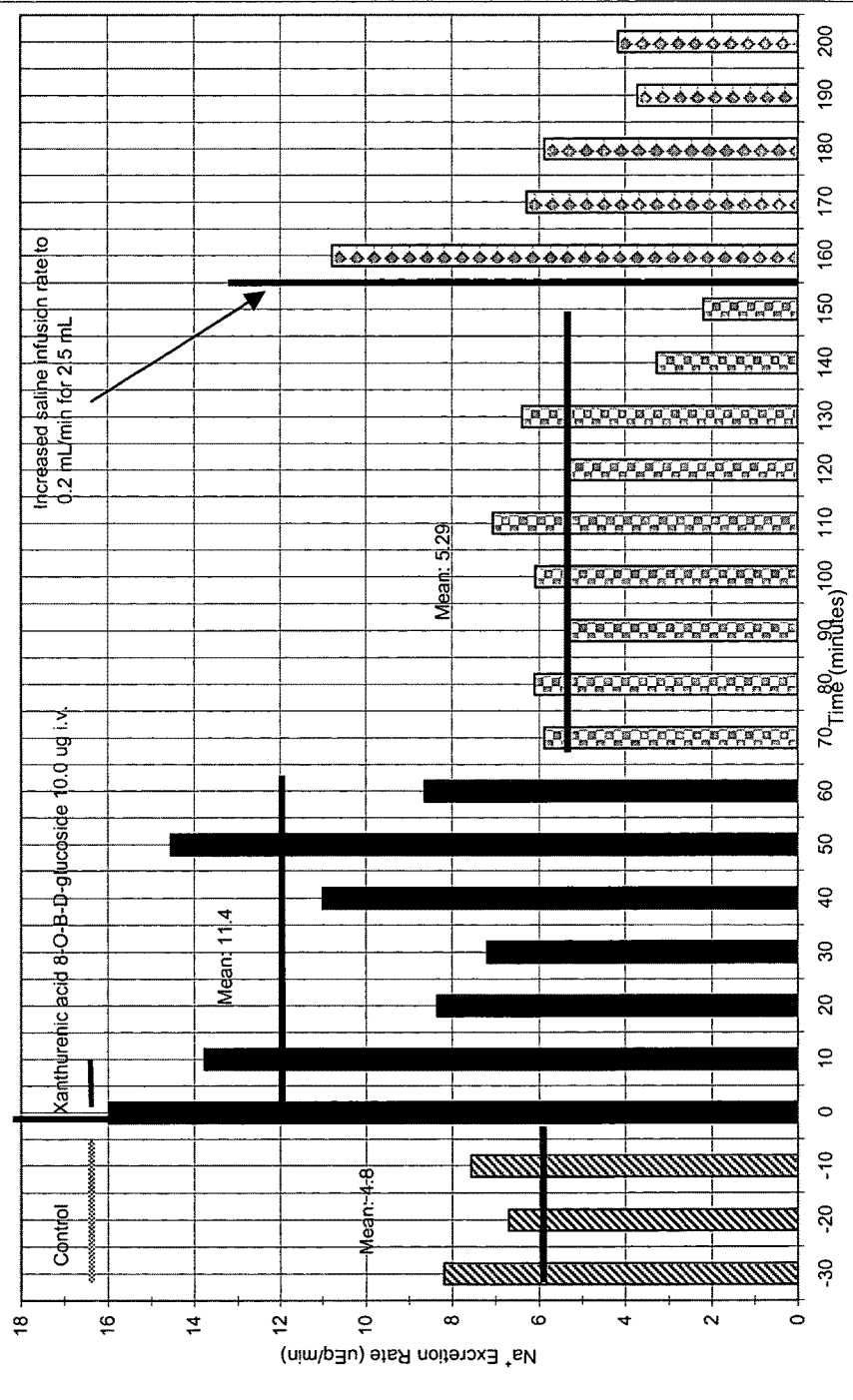
FIG. 5 shows Na$^+$ excretion in response to i.v. administration (10 µg dose) of synthetic xanthurenic acid 8-O-ß-D-glucoside in a normal Sprague Dawley rat.
Figure 6:
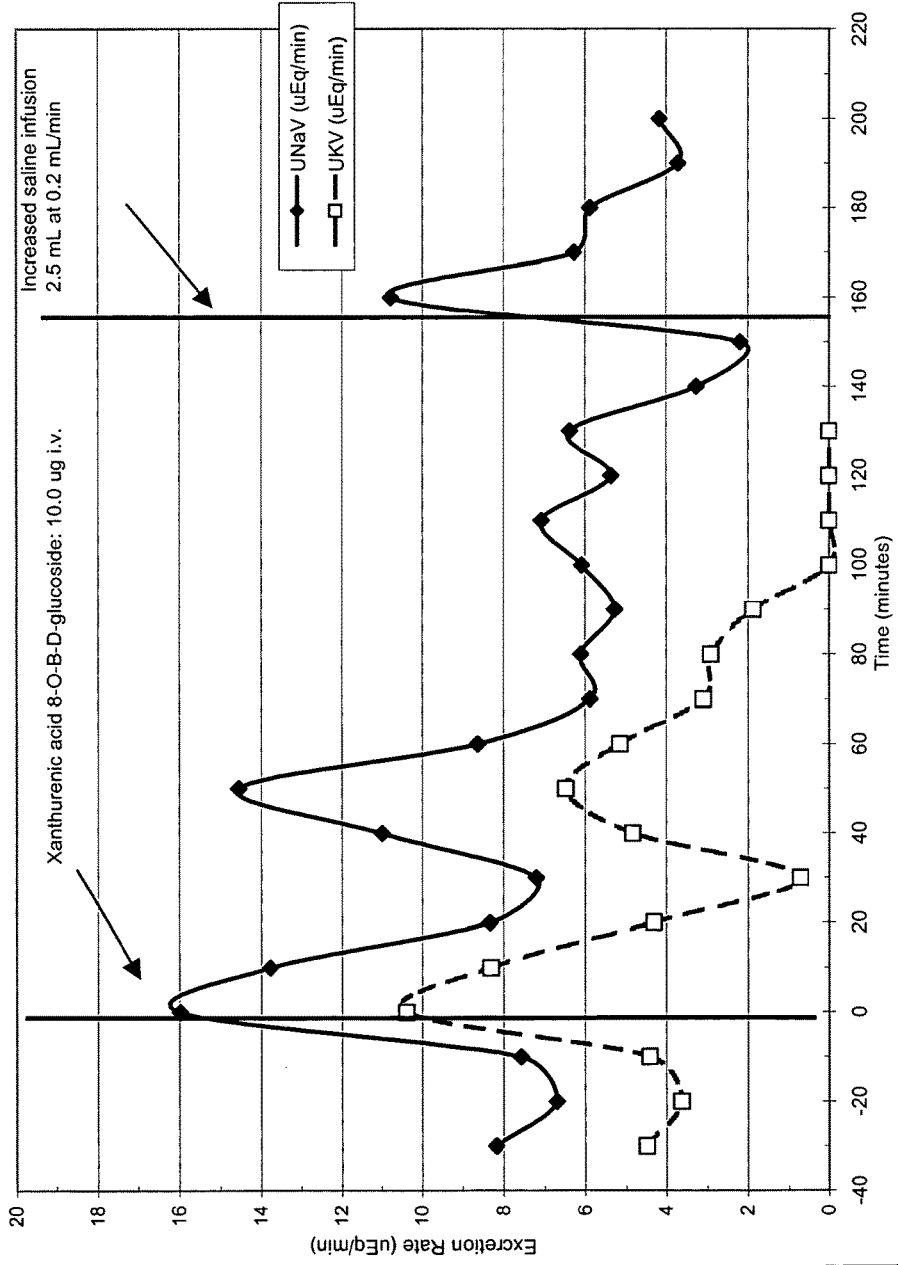
FIG. 6 shows Na$^+$ and K$^+$ urine excretion in response to i.v. administration (10 µg dose) of synthetic xanthurenic acid 8-O-ß-D-glucoside in a normal Sprague Dawley rat.

Example 4. Natriuretic Response to Synthetic Xanthurenic Acid 8-O-β-D-Glucoside (2 µg i.v.) in a Normal Sprague Dawley Rat A female Sprague Dawley rat (250 g) was anesthetized lightly with ether and a tail vein catheter was placed using PE10 tubing. Additionally, a urethra catheter was inserted using KY jelly and 2% lidocaine as a lubricant. The rat was restrained in a modified Plexiglas tube so that urine could be collected in 1.5-mL microcentrifuge tubes. Saline infusion started at time zero at 0.02 mL/min for the duration of the assay. The same i.v. catheter was used to inject the test compound. Synthetic xanthurenic acid 8-O-ß-D-glucoside, 2 µg, was injected at the time indicated in a 1-mL volume in saline over the course of 10 minutes. The tubes were centrifuged at 14,000 rpm to separate any RBC's from the urine. $Na^+$ and $K^+$ concentrations in the urine were measured with respective ion selective electrodes. The $Na^+$ and $K^+$ excretion rates were calculated by: (vol of urine time of collection period)×(ion urine concentration). Results are shown in FIGS. 1-4. Synthetic xanthurenic acid 8-O-ß-D-glucoside at 2 ug i.v. caused a sustained natriuretic response in a normal rat. $Na^+$ excretion was due more to increased $Na^+$ urine concentration than increased urine volume as shown in FIGS. 3 and 4. Given an extracellular volume of 50 mL in a 250-g rat, the concentration of the test compound was $10^{-6}$ M, a possible minimum dose. In a similar experiment; synthetic, underivatized xanthurenic acid at 2 ug i.v. did not increase $Na^+$ excretion. However, subsequent administration of synthetic xanthurenic acid 8-O-ß-D-glucoside did cause natriuresis.

Figure 7:
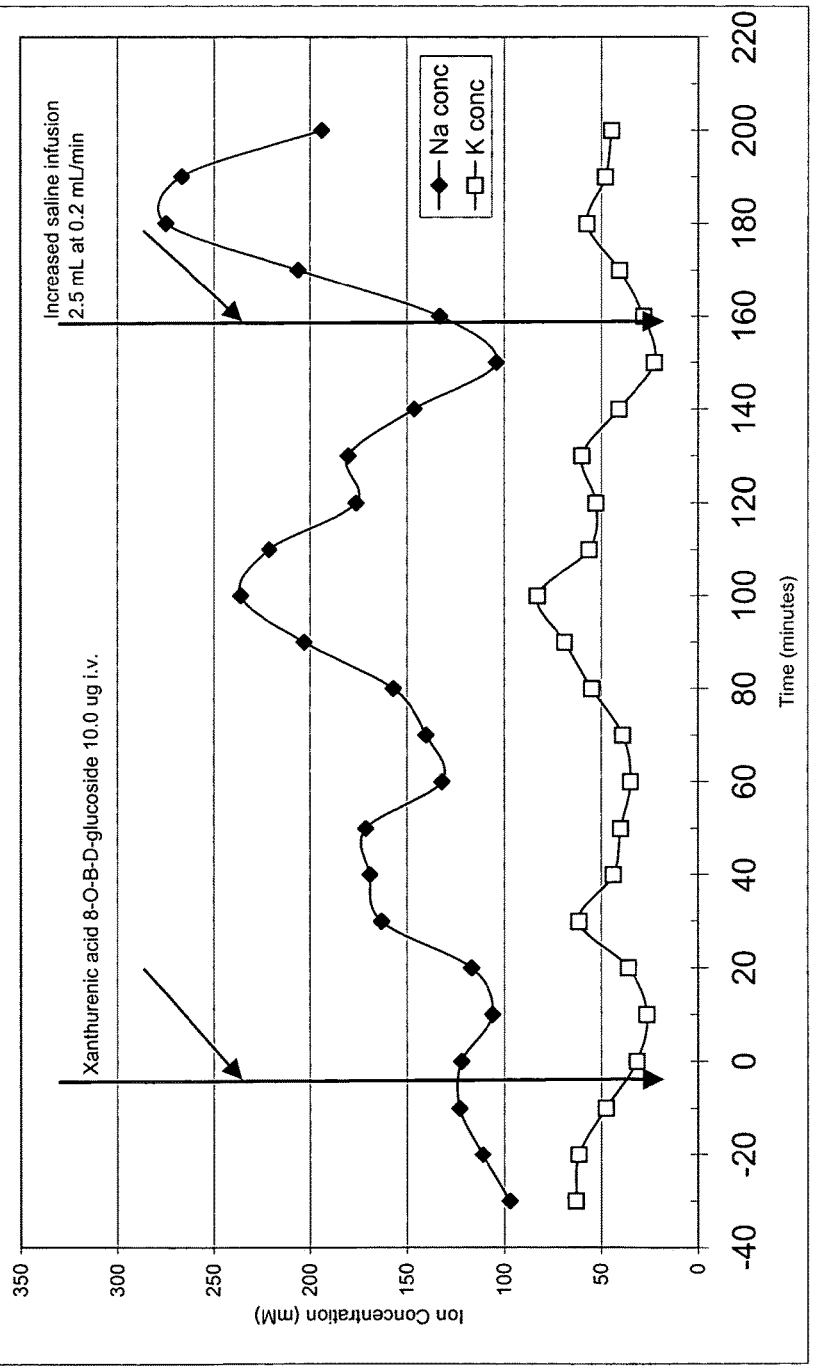
FIG. 7 shows Na$^+$ and K$^+$ concentration in urine in response to i.v. administration (10 µg dose) of synthetic xanthurenic acid 8-O-ß-D-glucoside in a normal Sprague Dawley rat.
Figure 8:
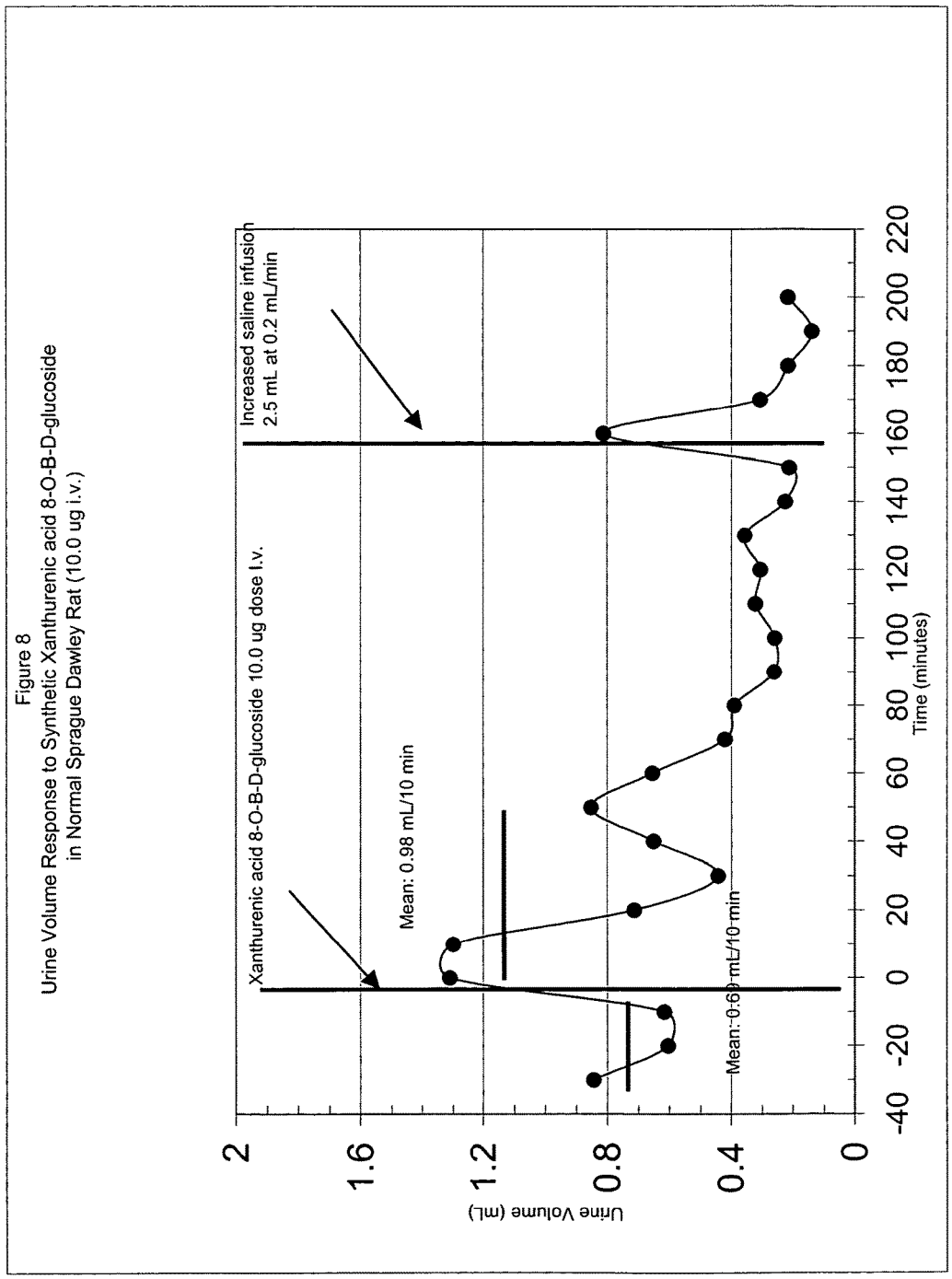
FIG. 8 shows urine volume following i.v. administration (10 µg dose) of synthetic xanthurenic acid 8-O-ß-D-glucoside in a normal Sprague Dawley rat.
Figure 9:
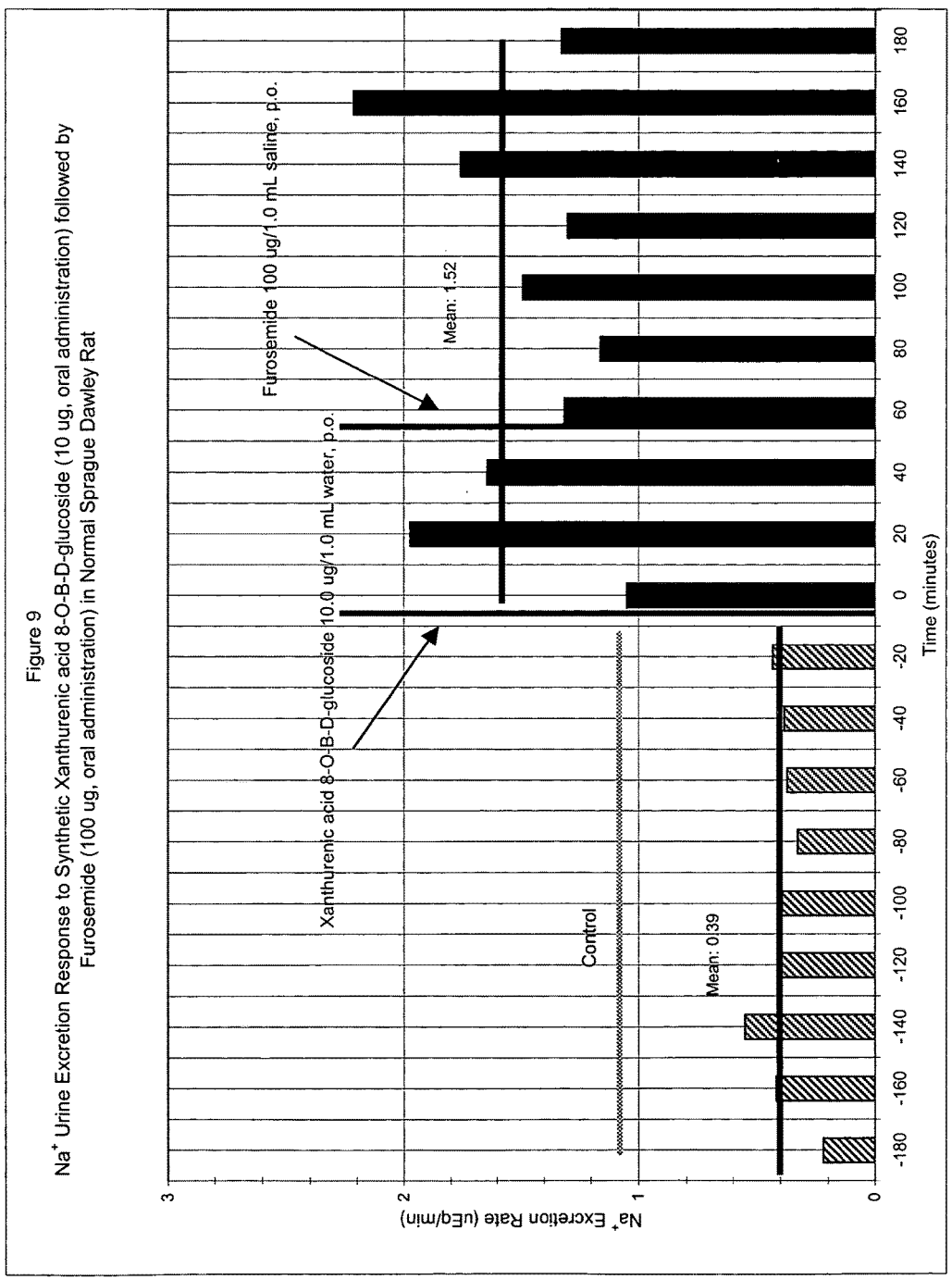
FIG. 9 shows Na$^+$ urine excretion in response to synthetic xanthurenic acid 8-O-β-D-glucoside (10 µg) followed by furosemide (100 µg) in a normal Sprague Dawley Rat, oral (p.o.) administration.
Figure 10:
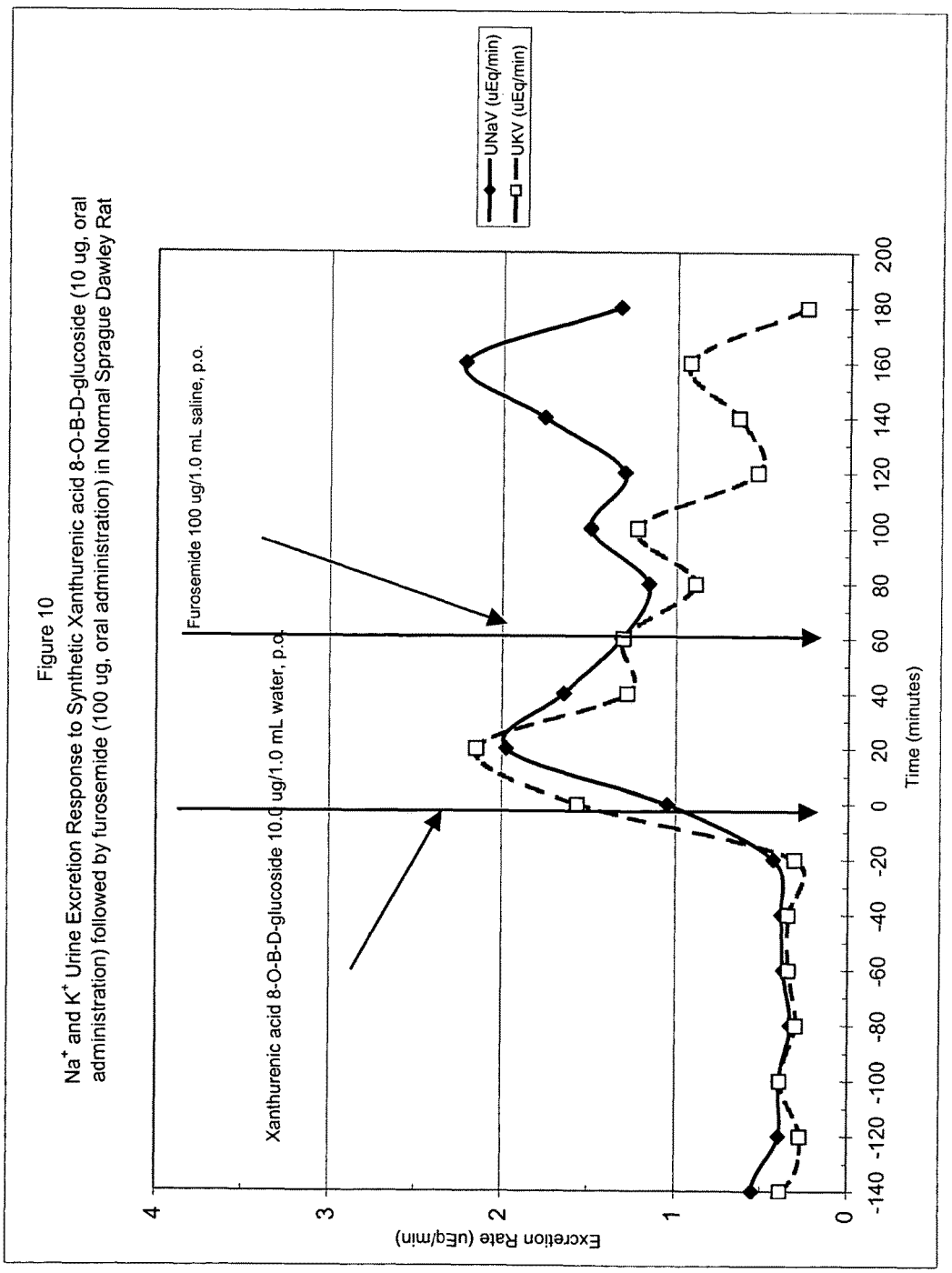
FIG. 10 shows Na$^+$ and K$^+$ urine excretion in response to synthetic xanthurenic acid 8-O-β-D-glucoside (10 µg) followed by furosemide (100 µg) in a normal Sprague Dawley Rat, oral (p.o.) administration.
Figure 11:
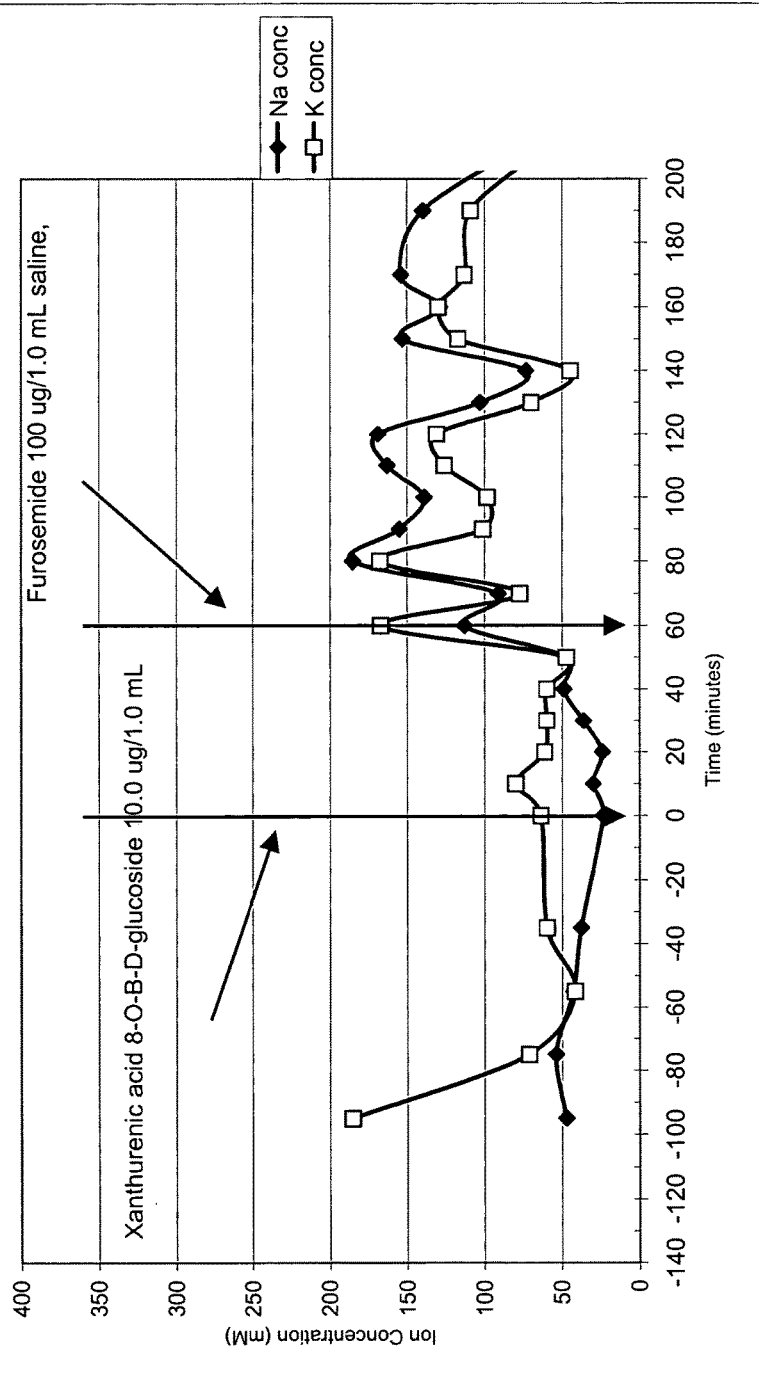
FIG. 11 shows Na$^+$ and K$^+$ concentration in urine in response to synthetic xanthurenic acid 8-O-β-D-glucoside (10 µg) followed by furosemide (100 µg) in a normal Sprague Dawley Rat, oral (p.o.) administration.
Figure 12:
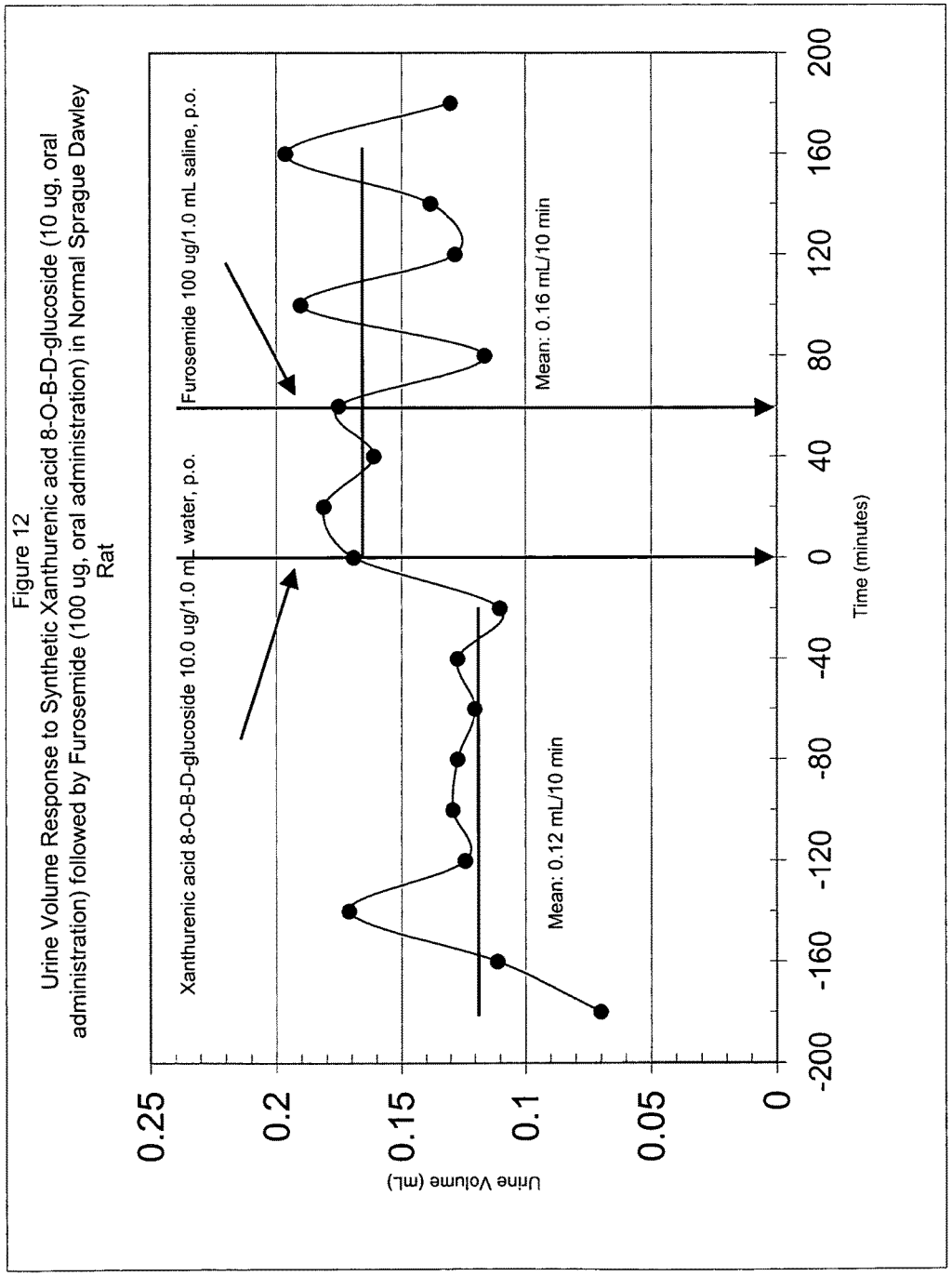
FIG. 12 shows urine volume following administration of synthetic xanthurenic acid 8-O-β-D-glucoside (10 µg) followed by furosemide (100 µg) in a normal Sprague Dawley Rat, oral (p.o.) administration.
Figure 13:
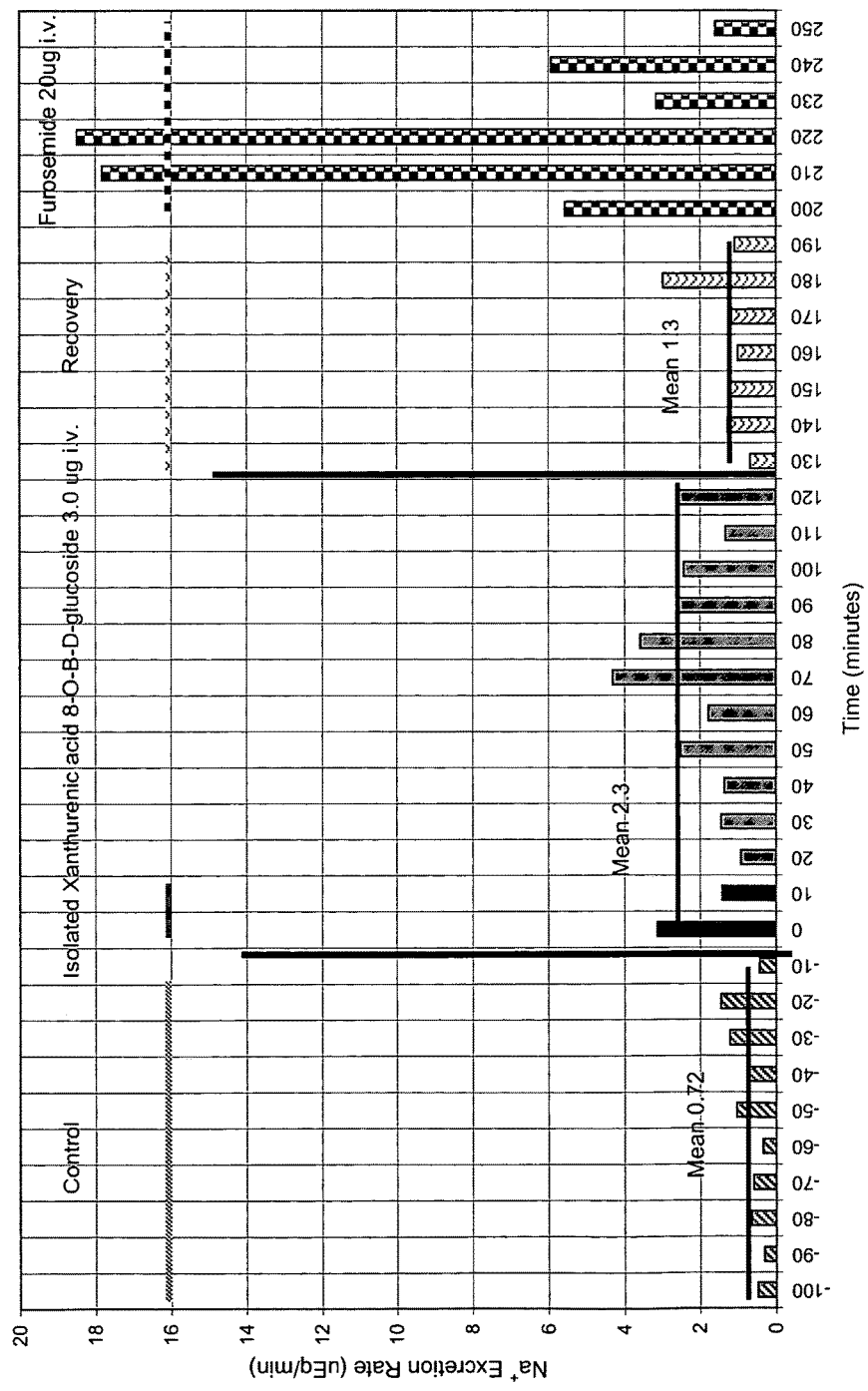
FIG. 13 shows Na$^+$ urine excretion in response to isolated xanthurenic acid 8-O-β-D-glucoside (3 µg) followed by furosemide (20 µg) in a uremic Sprague Dawley rat, i.v. administration.
Figure 14:
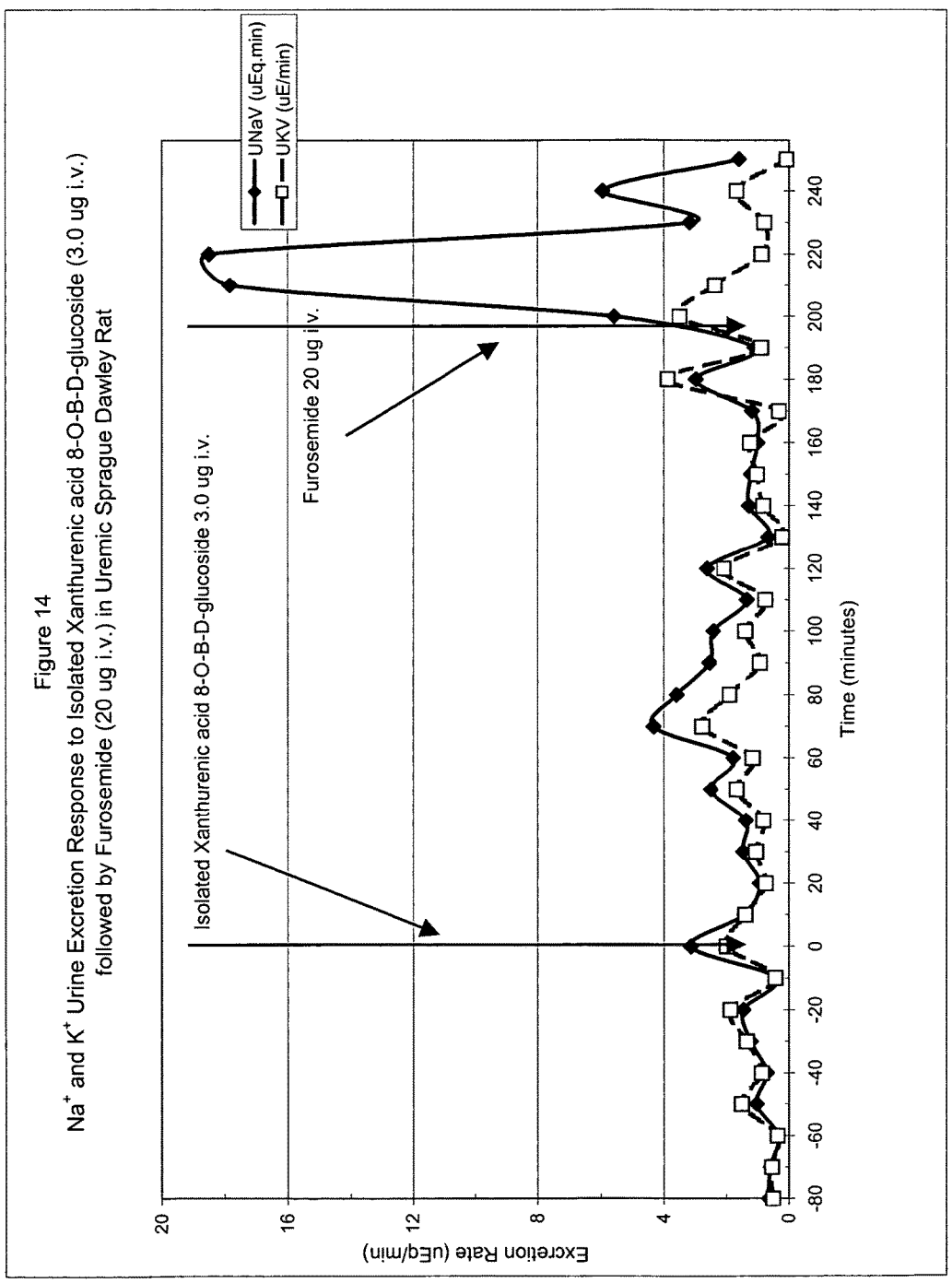
FIG. 14 shows Na$^+$ and K$^+$ urine excretion in response to isolated xanthurenic acid 8-O-β-D-glucoside (3 µg) followed by furosemide (20 µg) in a uremic Sprague Dawley rat, i.v. administration.
Figure 15:
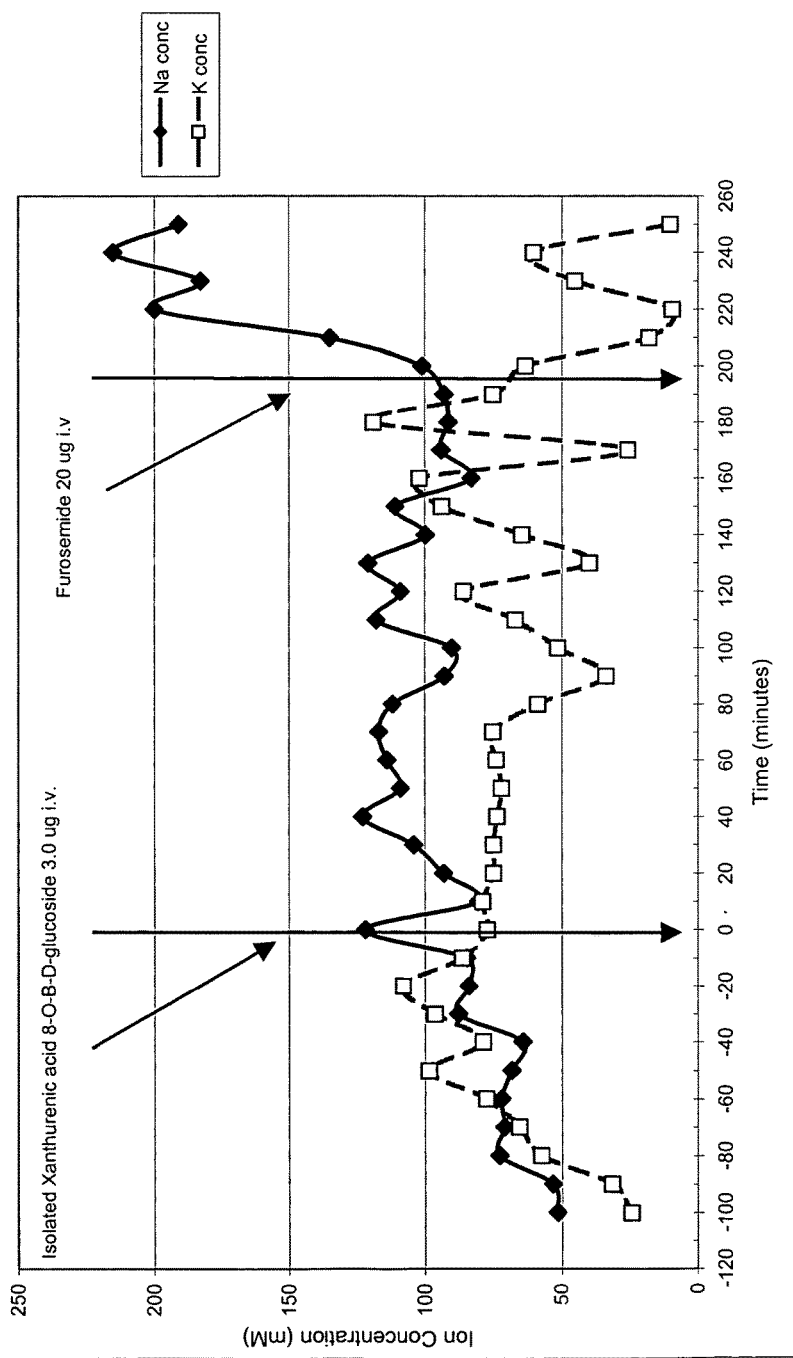
FIG. 15 shows Na$^+$ and K$^+$ urine concentration in urine in response to isolated xanthurenic acid 8-O-β-D-glucoside (3 µg) followed by furosemide (20 µg) in a uremic Sprague Dawley rat, i.v. administration.
Figure 16:
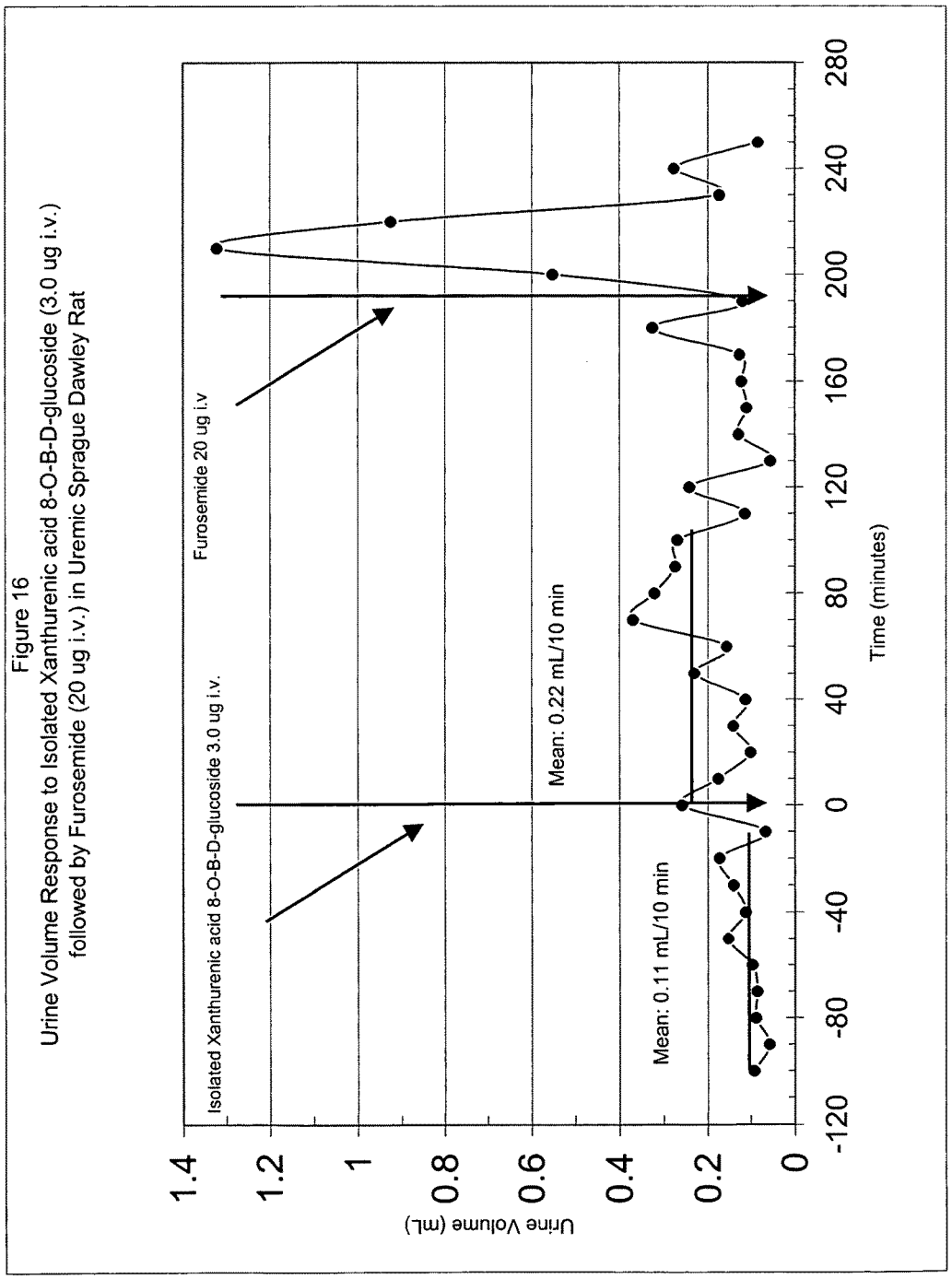
FIG. 16 shows urine volume in response to isolated xanthurenic acid 8-O-β-D-glucoside (3 µg) followed by furosemide (20 µg) in a uremic Sprague Dawley rat, i.v. administration.
Figure 17:
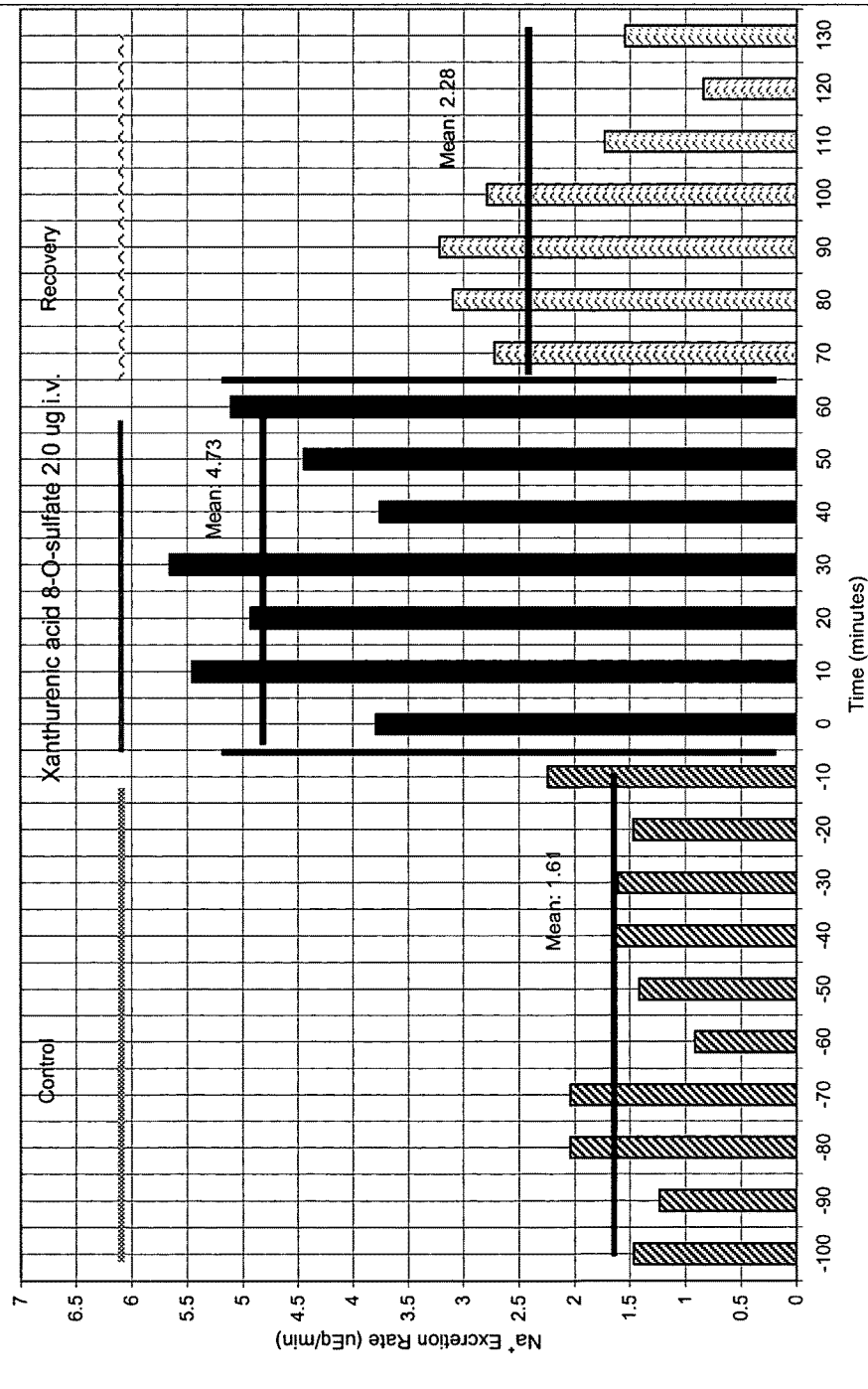
FIG. 17 shows Na$^+$ urine excretion in response to isolated xanthurenic acid 8-O-sulfate (2 µg) in uremic Sprague Dawley rat, i.v. administration.
Figure 18:
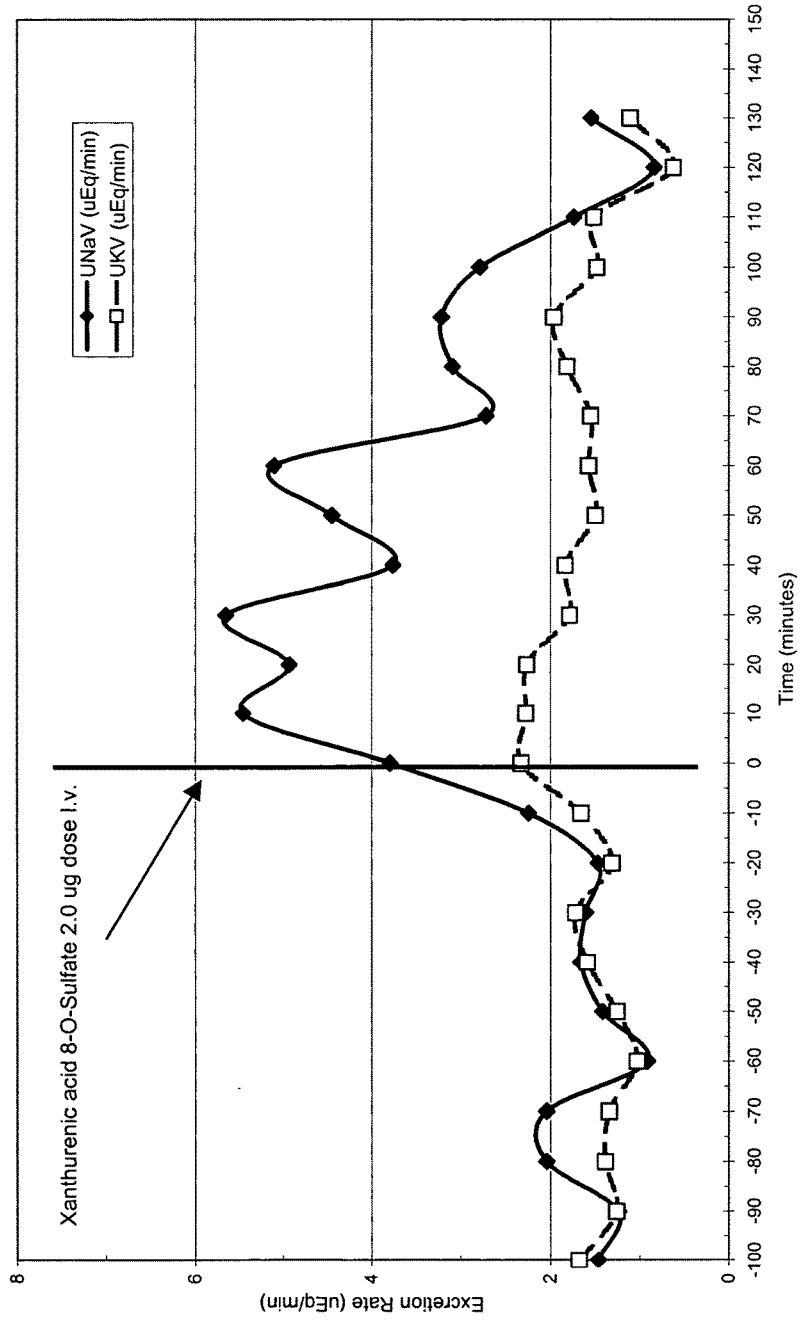
FIG. 18 shows Na$^+$ and K$^+$ urine excretion in response to isolated xanthurenic acid 8-O-sulfate (2 µg) in uremic Sprague Dawley rat, i.v. administration.
Figure 19:
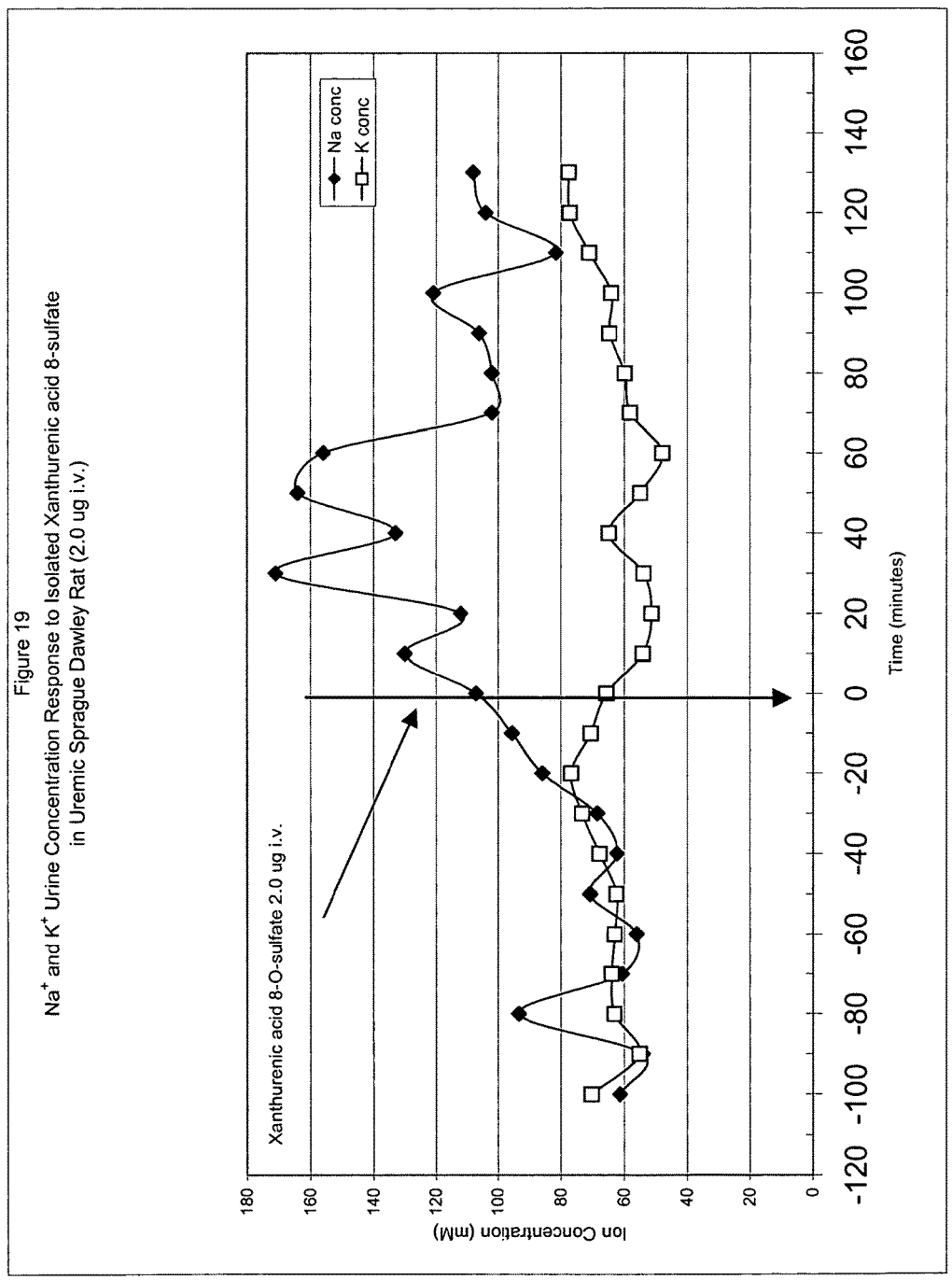
FIG. 19 shows Na$^+$ and K$^+$ urine concentration in urine in response to isolated xanthurenic acid 8-O-sulfate (2 µg) in uremic Sprague Dawley rat, i.v. administration.
Figure 20:
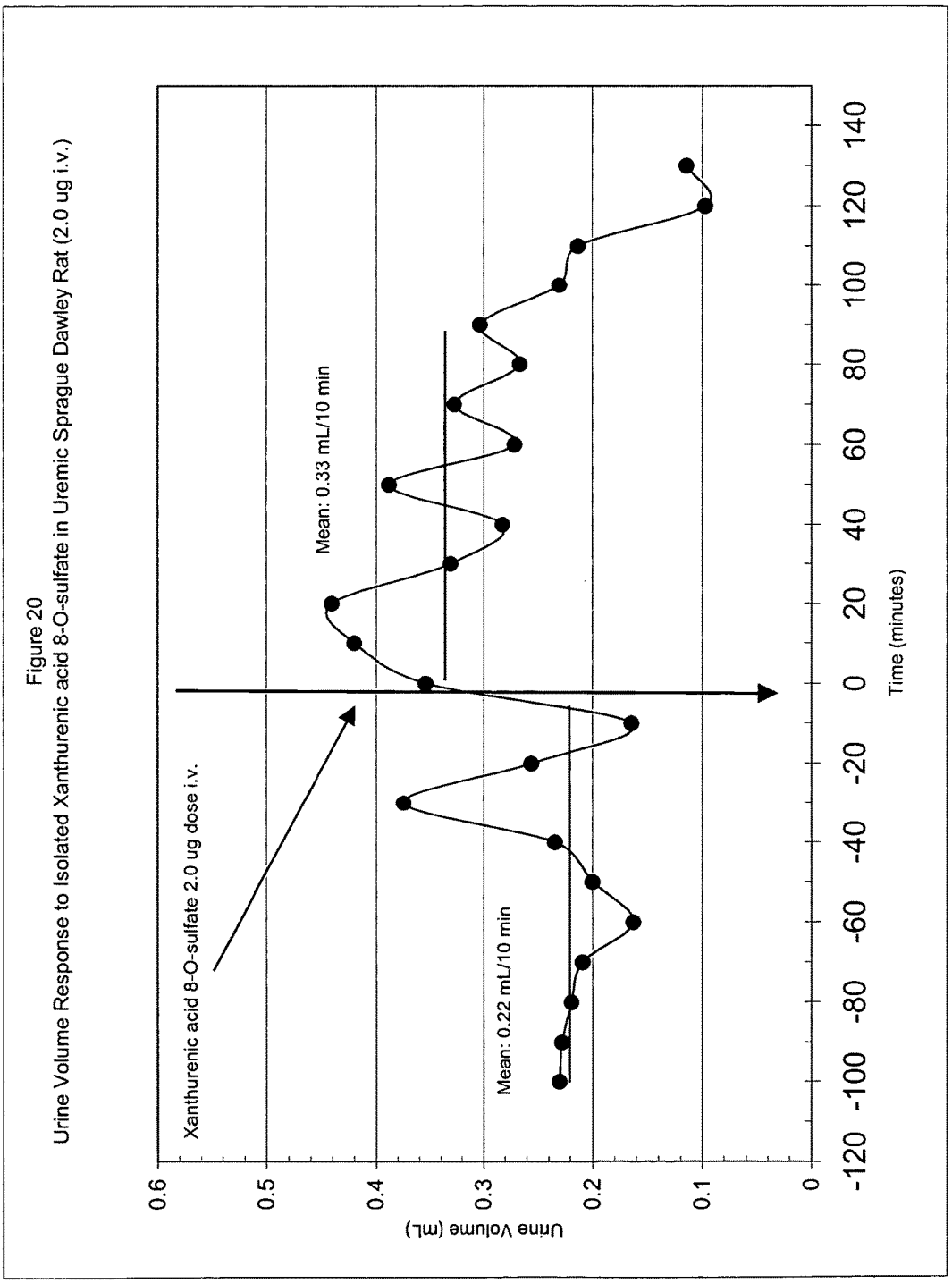
FIG. 20 shows urine volume in response to isolated xanthurenic acid 8-O-sulfate (2 µg) in uremic Sprague Dawley rat, i.v. administration.
Figure 21:
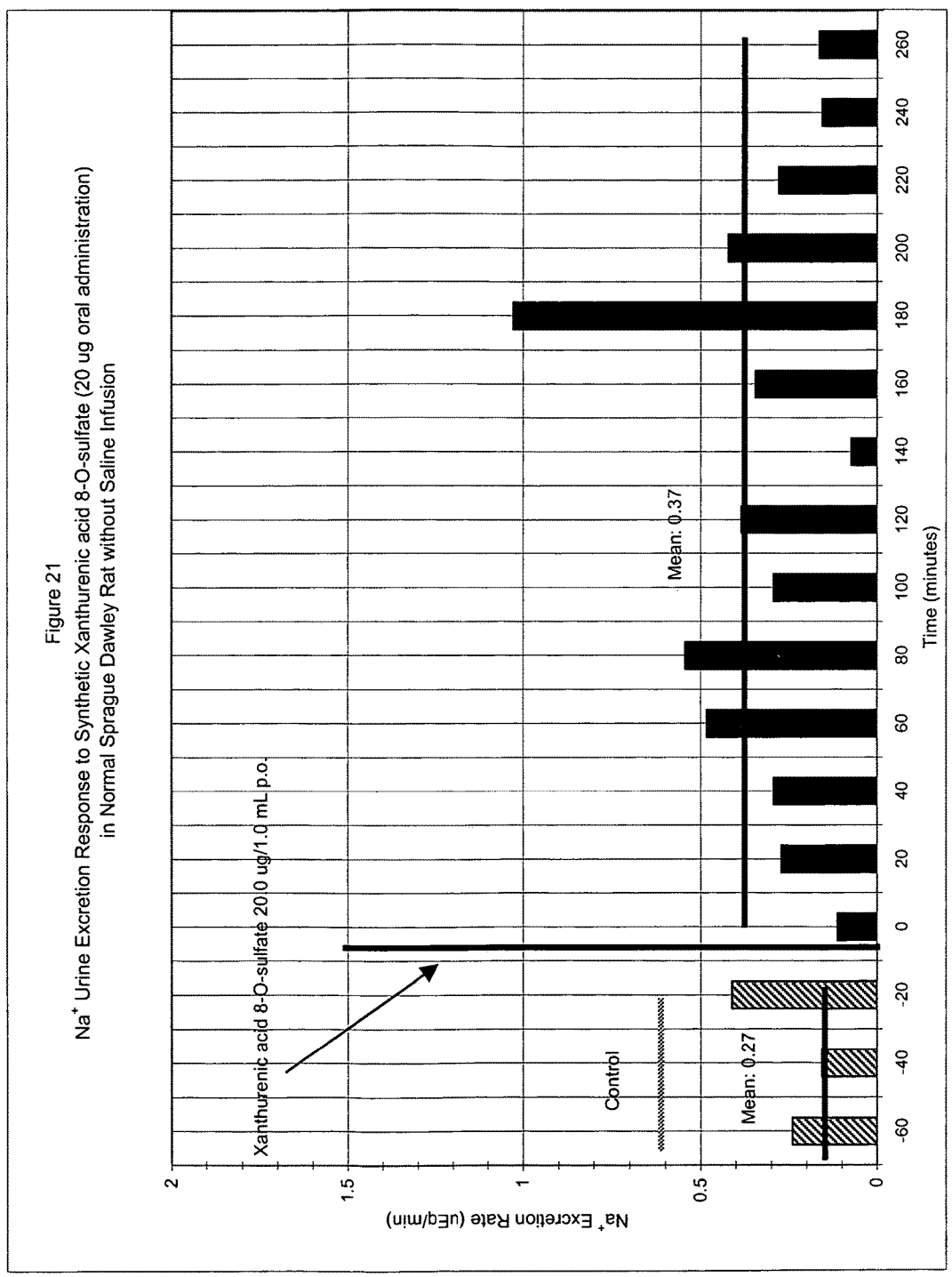
FIG. 21 shows Na$^+$ urine excretion in response to synthetic xanthurenic acid 8-O-sulfate (20.0 µg) in normal Sprague Dawley rat by oral administration.
Figure 22:
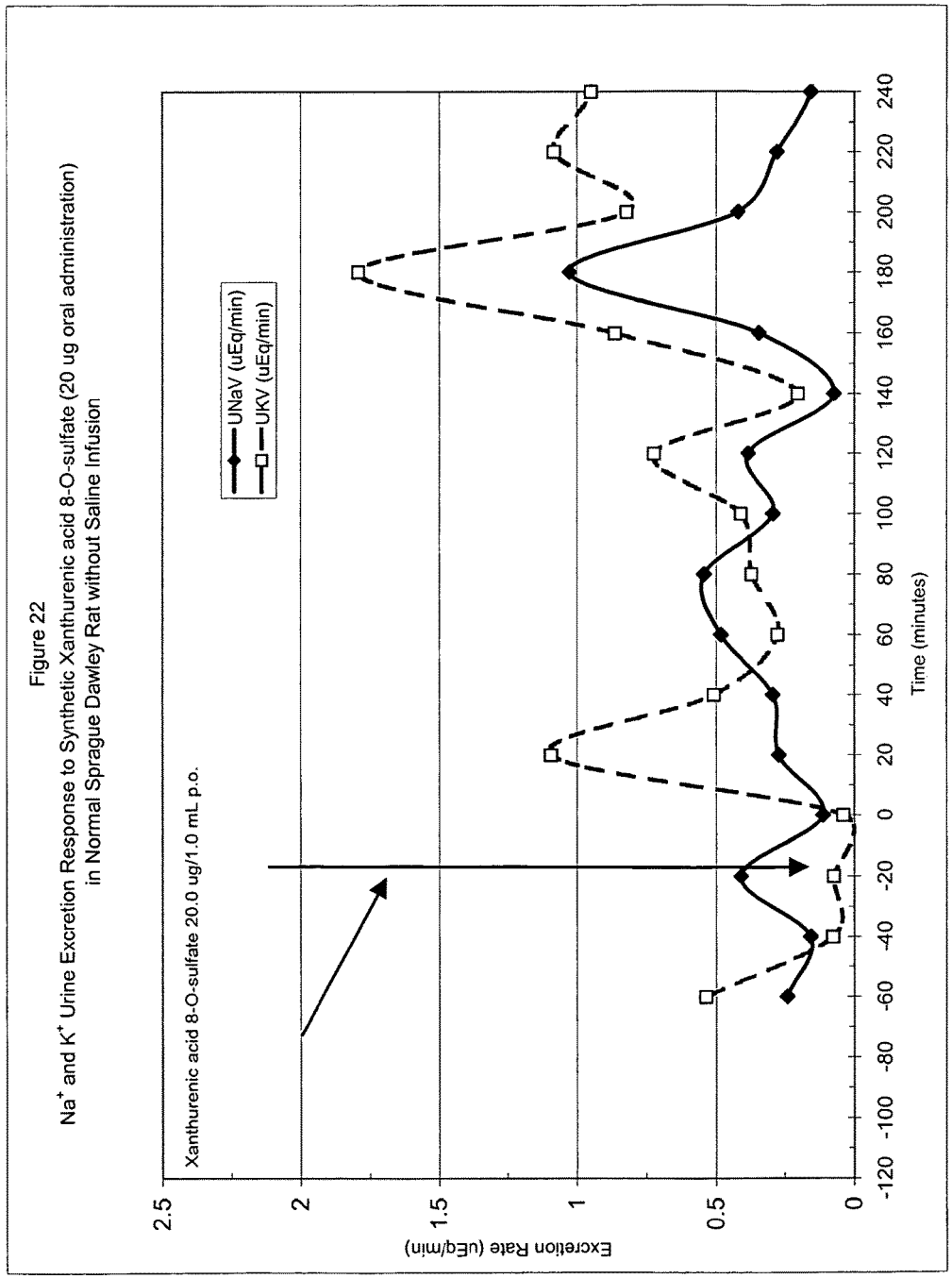
FIG. 22 shows Na$^+$ and K$^+$ urine excretion in response to synthetic xanthurenic acid 8-O-sulfate (20.0 µg) in normal Sprague Dawley rat by oral administration.
Figure 23:
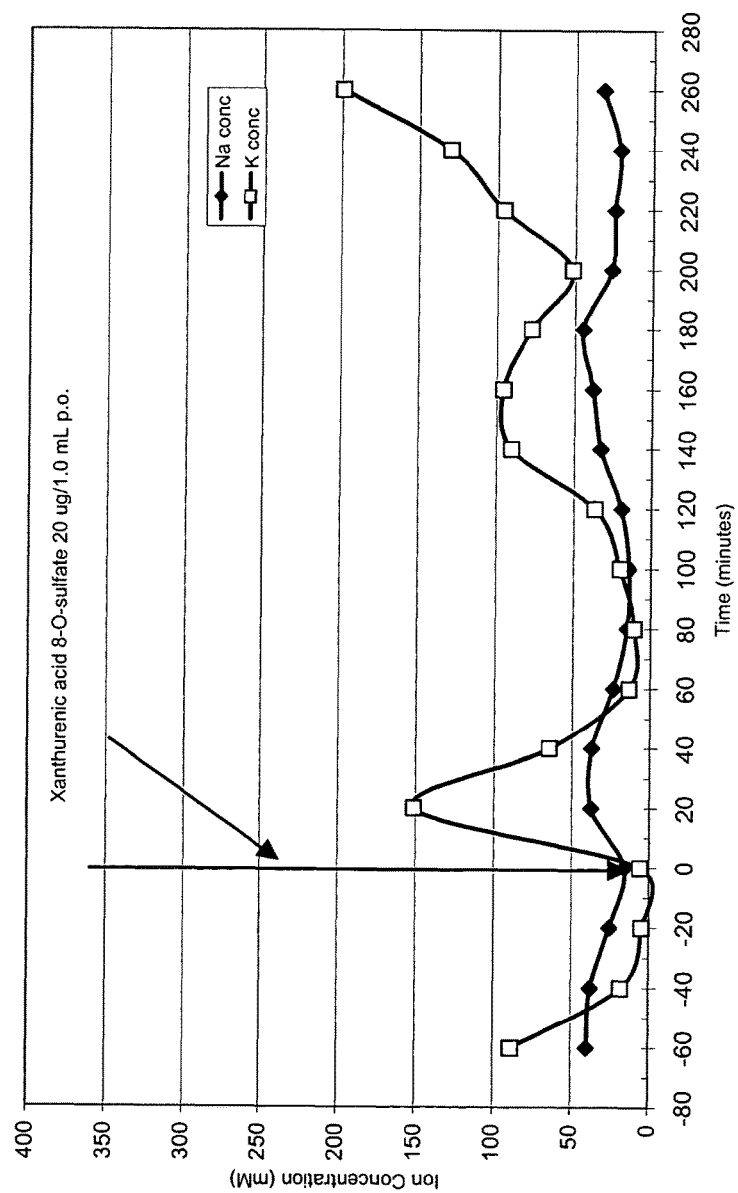
FIG. 23 shows Na$^+$ and K$^+$ concentration in urine in response to synthetic xanthurenic acid 8-O-sulfate (20.0 µg) in normal Sprague Dawley rat by oral administration.
Figure 24:
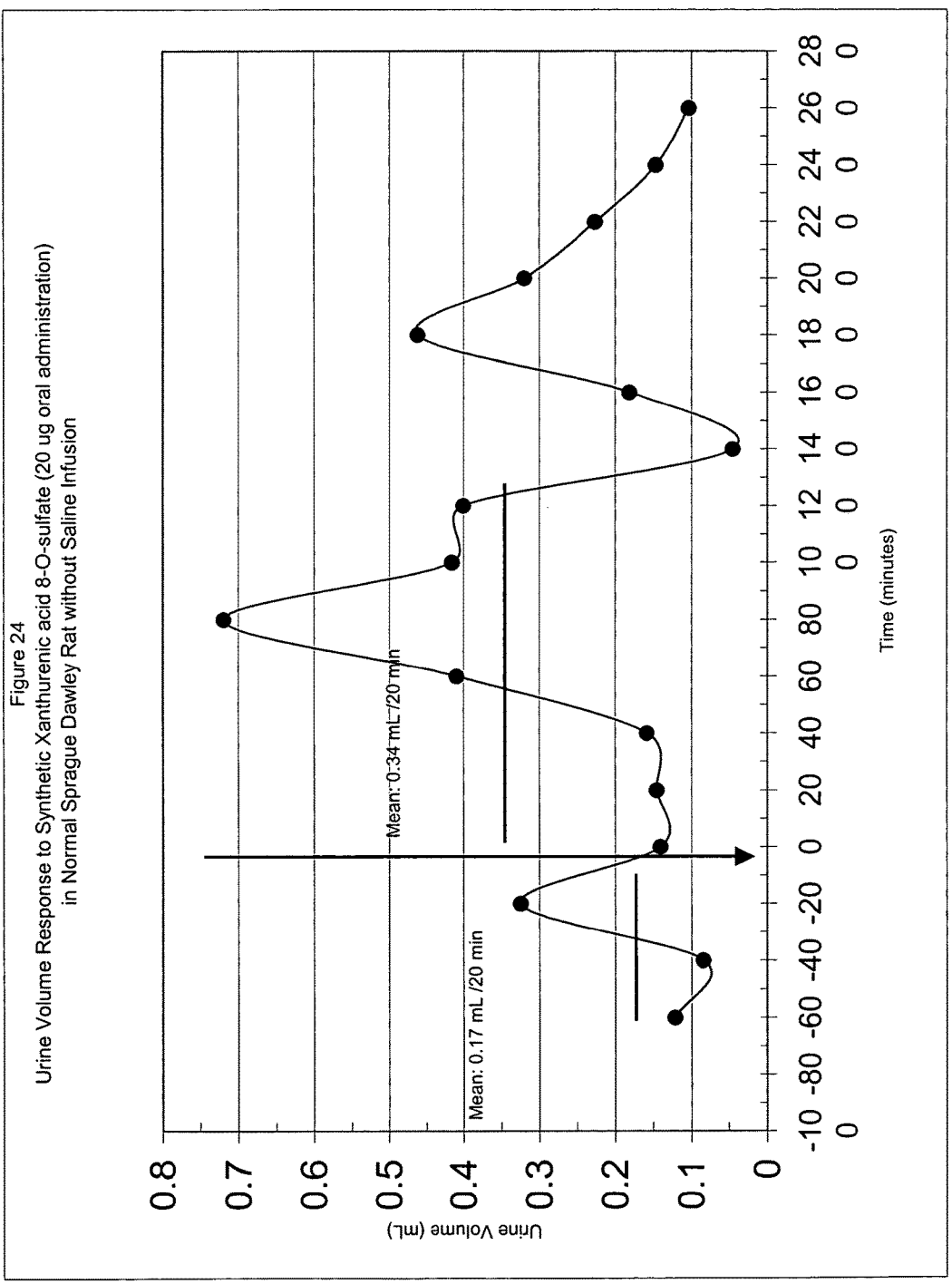
FIG. 24 shows urine volume in response to synthetic xanthurenic acid 8-O-sulfate (20.0 µg) in normal Sprague Dawley rat by oral administration.

Example 5. Natriuretic Response to Synthetic Xanthurenic Acid 8-O-ß-D-Glucoside (10 µg i.v.) in a Normal Sprague Dawley Rat A female Sprague Dawley rat (250 g) was anesthetized lightly with ether and a tail vein catheter was placed using PE10 tubing. Additionally, a urethra catheter was inserted using KY jelly and 2% lidocaine as a lubricant. The rat was restrained in a modified Plexiglas tube so that urine could be collected in 1.5-mL microcentrifuge tubes. Saline infusion started at time zero at 0.02 mL/min for the length of the assay. The same i.v. catheter was used to inject the test compound. Synthetic xanthurenic acid 8-O-ß-D-glucoside, 10 µg i.v. was injected at the time indicated in a 1-mL volume in saline over the course of 10 minutes. At the indicated time the saline infusion was increased tenfold to 0.2 mL/min for ten minutes and returned to 0.02 mL/min for the duration of the assay. The tubes were centrifuged at 14,000 rpm to separate any RBC's from the urine. $Na^+$ and $K^+$ concentrations in the urine were measured with respective ion selective electrodes. The $Na^+$ and $K^+$ excretion rates were calculated by (vol of urine time of collection period)×(ion urine concentration). Results are shown in FIGS. 5-8. Synthetic xanthurenic acid 8-O-ß-D-glucoside at 10 µg i.v. caused a sustained natriuretic response in the normal rat. $K^+$ excretion did not increase in response to xanthurenic acid 8-O-ß-D-glucoside. The initial natriuretic response in FIG. 6 (10-20 min) was due to the increase in urine volume shown in FIG. 8, and not due to urine $Na^+$ concentration shown in FIG. 7. However by 60-90 minutes after administration the natriuresis was due to the increased urine $Na^+$ concentration as shown in FIG. 7.

Urine production decreased 140 min after administration resulting in decreased natriuresis. However when the saline infusion increased to tenfold to 0.2 mL/min for 10 minutes, $Na^+$ excretion rate increased from 2 uEq/min to 10 uEq/min, seen in FIG. 6. These data are consistent with the idea that xanthurenic acid 8-O-ß-D-glucoside inhibited $Na^+$ reabsorption at the distal tubule causing $Na^+$ excretion but only if hydration and GFR were sufficient for enough fluid to reach the distal tubule.

Example 6. Natriuretic Response to Synthetic Xanthurenic Acid 8-O-B-D-Glucoside (10 µg) Followed by Furosemide (100 µg) in a Normal Sprague Dawley Rat, (Oral Administration)

A female Sprague Dawley rat (250 g) was anesthetized lightly with ether and a urethra catheter was inserted using KY jelly and 2% lidocaine as a lubricant. The rat was restrained in a modified Plexiglas tube so that urine could be collected in 1.5-mL microcentrifuge tubes. No saline infusion was administered. Synthetic xanthurenic acid 8-O-ß-D-glucoside was injected with a feeding needle at the time indicated in a 1-mL volume of water over the course of 1 minute. Sixty minutes later 100 µg of furosemide was similarly administered with a feeding needle. The tubes were centrifuged at 14,000 rpm to separate any RBC's from the urine. $Na^+$ and $K^+$ concentrations in the urine were measured with respective ion selective electrodes. The $Na^+$ and $K^+$ excretion rates were calculated by: (vol of urine/time of collection period)×(ion urine concentration). Results are shown in FIGS. 9-12. Synthetic xanthurenic acid 8-O-ß-D-glucoside (10 µg) was orally active by causing a natriuretic response in a normal rat. Sixty minutes after oral administration, furosemide (100 µg) caused sustained $Na^+$ excretion seen in FIGS. 9-11. Pretreatment with xanthurenic acid 8-O-ß-D-glucoside followed by furosemide allowed increased $Na^+$ excretion, but did not increase $K^+$ excretion in FIG. 10. Oral furosemide alone caused both $Na^+$ and $K^+$ excretion (data not shown). Pretreatment with xanthurenic acid 8-O-ß-D-glucoside inhibited furosemide-induced $K^+$ excretion.

Example 7. Natriuretic Response to Isolated Xanthurenic Acid 8-O-B-D-Glucoside (3 µg) Followed by Furosemide (20 µg) in Uremic Sprague Dawley Rat (i.v.)

Female Sprague-Dawley rat, weighing 225 g, was made uremic by tying off one kidney and 30-50% of the second kidney. Two weeks later the rat was ready to test for natriuretic activity. The rat was anesthetized lightly with ether and a tail vein catheter was placed using PE10 tubing. Additionally, a urethra catheter was inserted using KY jelly and 2% lidocaine as a lubricant. The rat was restrained in a modified Plexiglas tube so that urine could be collected in 1.5-mL microcentrifuge tubes. Saline infusion started at time zero at 0.02 mL/min for the length of the assay. The same i.v. catheter was used to inject isolated xanthurenic acid 8-O-ß-glucoside at the time indicated in a 1-mL volume in saline over the course of 10 minutes. After 2 hours 20 ug furosemide was injected in the same manner. The tubes were centrifuged at 14,000 rpm to separate any RBC's from the urine. $Na^+$ and $K^+$ concentrations in the urine were measured with respective ion selective electrodes. The $Na^+$ and $K^+$ excretion rates were calculated by: (vol of urine time of collection period)×(ion urine concentration).

Figure 25:
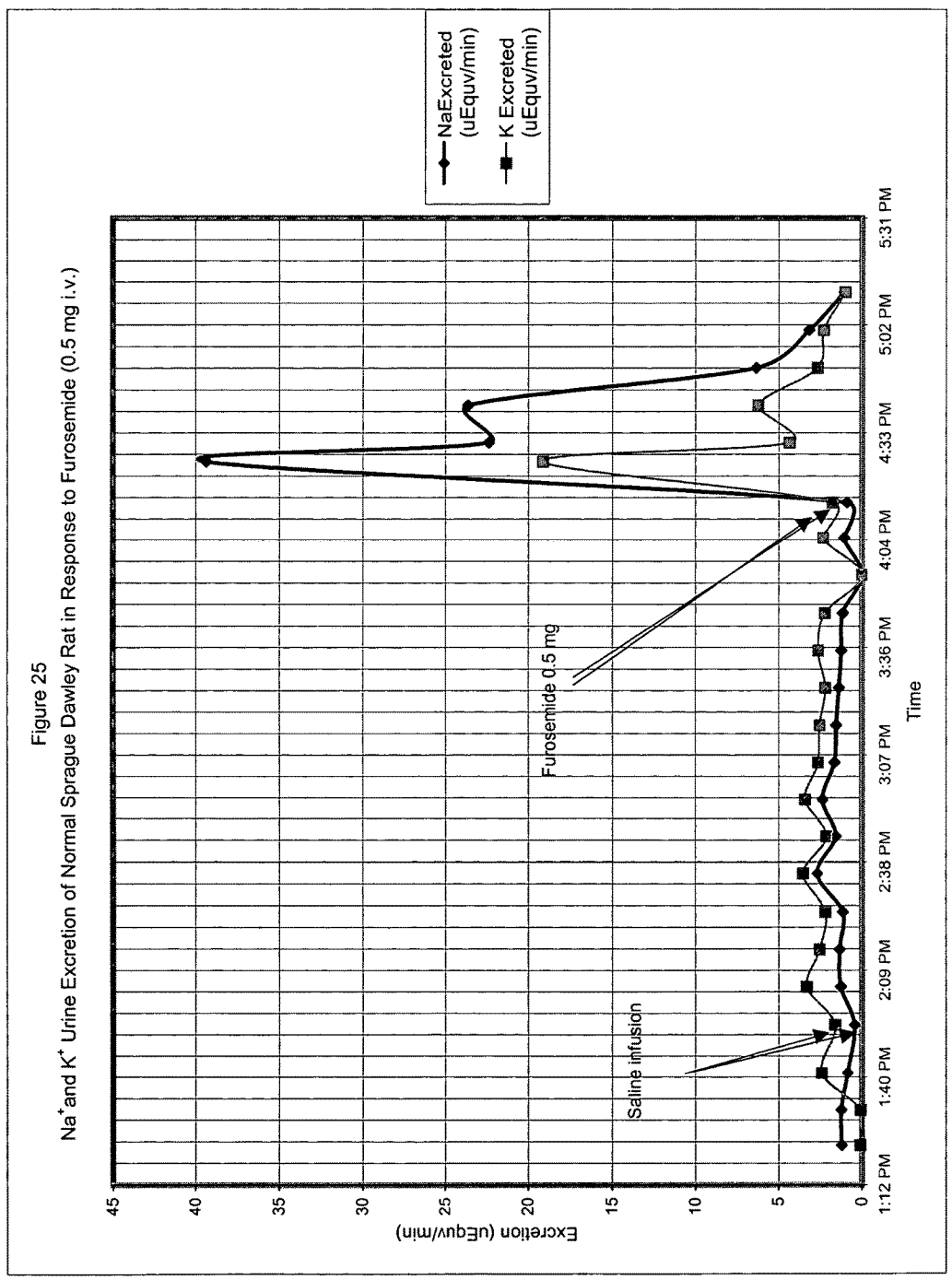
FIG. 25 shows Na$^+$ and K$^+$ urine excretion in normal Sprague Dawley rat in response to furosemide (0.5 mg, i.v.).
Figure 26:
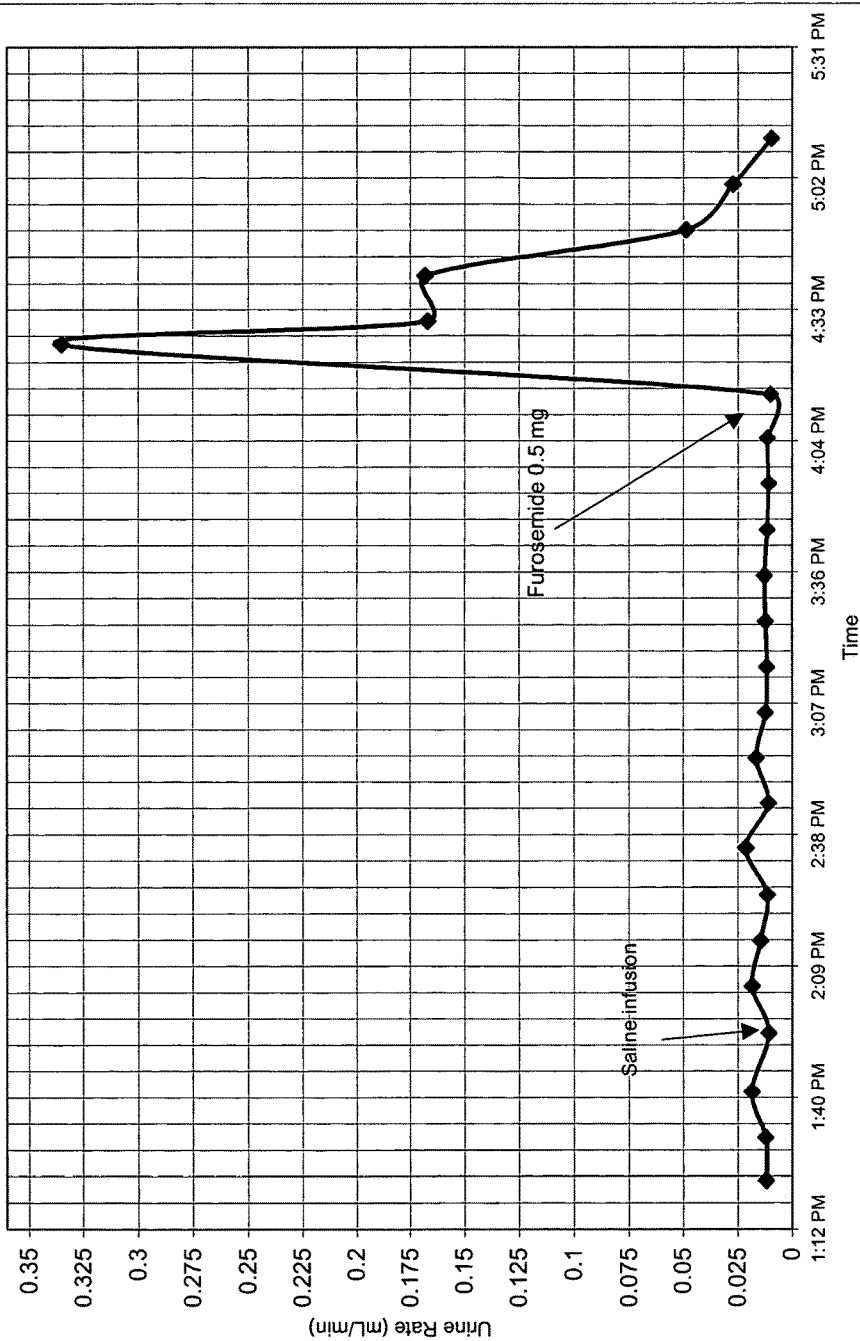
FIG. 26 shows urine excretion rate of normal Sprague Dawley rat in response to furosemide (0.5 mg i.v.).

Results are shown in FIGS. 13-16. Isolated xanthurenic acid 8-O-ß-D-glucoside at 3 µg i.v. caused a sustained natriuretic response in the uremic rat. The time course of $Na^+$ excretion peaked at 70 minutes in the uremic rat shown in FIG. 13, which is a similar time course to the synthetic xanthurenic acid 8-O-ß-glucoside in the normal rat shown in FIG. 1. $K^+$ excretion in FIGS. 14 and 15 did not increase in response to isolated xanthurenic acid 8-O-ß-glucoside. The diuretic response to furosemide was classic in terms of its time course as well as the $Na^+$ excretion. Normally, furosemide also causes $K^+$ excretion to the extent that $K^+$ supplementation is necessary in the clinical use of furosemide. A similar effect in normal rat is illustrated in FIG. 25 (furosemide only). Pretreatment with xanthurenic acid 8-O-ß-glucoside followed by furosemide prevented the typical increase in $K^+$ excretion in this assay shown in FIGS. 14 and 15.

Example 8. $Na^+$ and $K^+$ Urine Excretion Response to Isolated Xanthurenic Acid 8-O-Sulfate (2.0 µg) in Uremic Sprague Dawley Rat (i.v. Administration)

A female Sprague-Dawley rat, weighing 225 g, was made uremic by tying off one kidney and 30-50% of the second kidney. Two weeks later the rat was ready to test for natriuretic activity. The rat was anesthetized lightly with ether and a tail vein catheter was placed using PE10 tubing. Additionally, a urethra catheter was inserted using KY jelly and 2% lidocaine as a lubricant. The rat was restrained in a modified Plexiglas tube so that urine could be collected in 1.5-mL microcentrifuge tubes. Saline infusion started at time zero at 0.02 mL/min for the length of the assay. The same i.v. catheter was used to inject the test compound. Isolated Xanthurenic acid 8-O-sulfate, 2 µg, was injected at the time indicated in a 1 mL volume in saline over the course of 10 minutes. Then saline infusion was returned to 0.02 mL/min for the duration of the assay. The tubes were centrifuged at 14,000 rpm to separate any RBC's from the urine. $Na^+$ and $K^+$ concentrations in the urine were measured with respective ion selective electrodes. The $Na^+$ and $K^+$ excretion rates were calculated by: (vol of urine time of collection period)×(ion urine concentration).

Results are shown in FIGS. 17-20. Isolated xanthurenic acid 8-O-sulfate (2 µg, i.v.) caused sustained natriuretic response in the uremic rat. The time course of the natriuresis peaked within 30 minutes and then approached control levels within 70 minutes of treatment, seen in FIGS. 17 and 18. $K^+$ excretion did not increase in response to isolated xanthurenic acid 8-O-sulfate, shown in FIGS. 18 and 19.

Example 9. $Na^+$ and $K^+$ Urine Excretion Response to Synthetic Xanthurenic Acid 8-O-Sulfate (20 µg) in Normal Sprague Dawley Rat (Oral Administration)

A female Sprague Dawley rat (250 g) was anesthetized lightly with ether and a urethra catheter was inserted using KY jelly and 2% lidocaine as a lubricant. The rat was restrained in a modified Plexiglas tube so that urine could be collected in 1.5-mL microcentrifuge tubes. No saline infusion was administered. Xanthurenic acid 8-O-sulfate was injected with a feeding needle at the time indicated in a 1-mL volume of water over the course of 1 minute. The tubes were centrifuged at 14,000 rpm to separate any RBC's from the urine. $Na^+$ and $K^+$ concentrations in the urine were measured with respective ion selective electrodes. The $Na^+$ and $K^+$ excretion rates were calculated by: (vol of urine/time of collection period)×(ion urine concentration). Results are shown in FIGS. 21-24. Xanthurenic acid 8-O-sulfate (20 ug) was not orally active with respect to causing a natriuretic response in a normal rat. In particular, the $Na^+$ urine concentration remained below 50 mM in FIG. 21 whereas in i.v. administered xanthurenic acid 8-O-sulfate the $Na^+$ urine concentration increased from 60 mM to 160 mM in FIG. 19. In addition, Xanthurenic acid 8-O-ß-D-glucoside was orally active in a normal rat by increasing the $Na^+$ urine concentration to 160 mM in FIG. 11.

What is claimed is:

1. A pharmaceutical formulation comprising in unit dosage form a therapeutically effective amount of an acid or base salt of a freeze-dried, non-steroidal naturietic compound of formula (I):

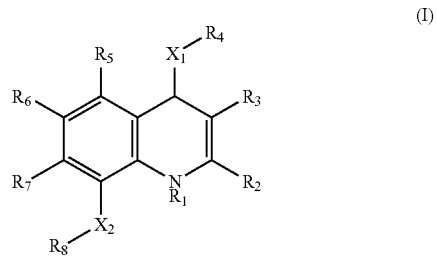

wherein $R_1$, $R_2$, $R_3$, $R_5$, $R_6$ and $R_7$ are independently $X_3R$ where R is selected from the group consisting of H, halo; optionally substituted saccharide, aliphatic, cycloalkyl, heterocycloalkyl, aryl and heteroaryl; —P(O)(OR$^a$)(OR$^b$) and —NR$^a$R$^b$, where R$^a$ and R$^b$ are independently H, optionally substituted aliphatic, cycloalkyl, heterocycloalkyl, aryl or heteroaryl;

$X_1$, and $X_3$ are independently —C(O)O—, —OC(O)—, —C(O)NH—, —NHC(O)—, OC(O)NH—, —NHC(O)O—, —OS(O)$_y$—, —S(O)$_y$—, —O—, —NHC(O)—, —NHC(O)O—, —S(O)$_2$NH—, a bond or absent; where y is an integer from 0 to 3; and $R_4$ is H, (=O); hydroxy; or optionally substituted saccharide, aliphatic, cycloalkyl, heterocycloalkyl, aryl or heteroaryl; or —P(O)(OR$^a$)(OR$^b$) or NR$^a$R$^b$, where R$^a$ and R$^b$ are independently H, or optionally substituted aliphatic, cycloalkyl or heterocycloalkyl, aryl or heteroaryl;

$X_2$ is —O— and $R_8$ is an optionally substituted saccharide; or $X_2$ is OS(O)$_y$— or S(O)$_y$—, where y is an integer from 0 to 3, and $R_8$ is H or optionally substituted aliphatic;

and a pharmaceutically acceptable carrier.

2. The formulation of claim 1 wherein $R_1$, $R_3$, $R_5$, $R_6$ and $R_7$ are independently H or halogen.

3. The formulation of claim 2 wherein $X_1$ is absent or a bond and $R_4$ is hydroxy or (=O).

4. The formulation of claim 3 wherein $R_2$ is —C(O)OR.

5. The formulation of claim 4 wherein $R_2$ is —C(O)OH.

6. The formulation of claim 1 wherein $R_8$ is an optionally substituted saccharide.

7. The formulation of claim 6 wherein $X_2$ is —O— and $R_8$ is an optionally substituted monosaccharide.

8. The formulation of claim 7 wherein $R_8$ is an aldohexopyranose, aldopentopyranose, aldopentofuranose or ketose.

9. The formulation of claim 8 wherein $R_8$ is a glucoside.

10. The formulation of claim 1 wherein the compound of formula I is xanthurenic acid 8-O-β-D-glucoside.

11. The formulation of claim 1 wherein $X_3$ is —OS(O)$_y$—.

12. The formulation of claim 1 wherein the compound of formula I is xanthurenic acid 8-O-sulfate.

13. The formulation of claim 1, further comprising a diuretic compound selected from the group consisting of a loop diuretic, thiazide diuretic, potassium-sparing diuretic, carbonic anhydrase inhibitor and osmotic diuretic.

14. The formulation of claim 13, wherein the diuretic compound is selected from furosemide, bumetanide, torsemide, ethacrynic acid, chlorothiazide, hydrochlorothiazide, spironolactone, amiloride, triamterene, acetazolamide, methazolamide, dichlorphenamide, hydroflumethiazide, methyclothiazide, indapamide, metolazone, polythiazide, chlorthalidone, dorzolamide, brinzolamide, glycerol, mannose and urea.

15. The formulation of claim 14, wherein the diuretic compound is furosemide.

16. The formulation of claim 1, further comprising a cardiovascular agent selected from the group consisting of an angiotensin converting enzyme inhibitor, angiotensin II receptor antagonist and beta-adrenergic blocker.

17. The formulation of claim 16, wherein the cardiovascular agent is lisinopril, moexipril, enalapril, irbesartan, valsartan, losartan, nadolol, propranolol, atenolol, timolol or bisoprolol.

18. A method of treating or controlling hypertension, edema, acute renal failure, congestive heart failure, chronic renal failure, ascites, increased intra-ocular pressure or nephrotic syndrome in a mammal, comprising administering a formulation of claim 1, orally or intravenously.

19. A method for effecting diuresis in a patient in need thereof, comprising administering a formulation of claim 1, orally or intravenously.

20. The method of claim 19, where said patient has one or more of the following conditions: hypertension, edema, acute renal failure, congestive heart failure, chronic renal failure, ascites, increased intra-ocular pressure or nephrotic syndrome.

* * * * *